(12) United States Patent
Bjorkholm

(10) Patent No.: US 7,257,188 B2
(45) Date of Patent: Aug. 14, 2007

(54) DUAL ENERGY RADIATION SCANNING OF CONTENTS OF AN OBJECT

(75) Inventor: Paul Bjorkholm, Newport Beach, NY (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/070,143

(22) Filed: Feb. 28, 2005

(65) Prior Publication Data

US 2007/0025505 A1 Feb. 1, 2007

Related U.S. Application Data

(60) Provisional application No. 60/568,541, filed on May 5, 2004, provisional application No. 60/549,093, filed on Mar. 1, 2004.

(51) Int. Cl.
*G01N 23/06* (2006.01)
*H05G 1/64* (2006.01)

(52) U.S. Cl. .................. 378/53; 378/57; 378/98.9

(58) Field of Classification Search ............... 378/4, 378/5, 9, 19, 57, 51, 98.9, 53, 156; 250/306, 250/307
See application file for complete search history.

(56) References Cited

U.S. PATENT DOCUMENTS

| | | | |
|---|---|---|---|
| 3,018,374 A | 1/1962 | Pritchett | |
| 3,636,353 A | 1/1972 | Untermyer | |
| 3,924,132 A | 12/1975 | Koslow | |
| 4,229,654 A | 10/1980 | Arya et al. | |
| 4,251,726 A | 2/1981 | Alvarez | |
| 4,382,208 A | 5/1983 | Meddaugh et al. | |
| 4,400,650 A | 8/1983 | Giebeler, Jr. | |
| 4,511,799 A | 4/1985 | Bjorkholm et al. | |
| 4,540,882 A * | 9/1985 | Vinegar et al. | .............. 250/255 |
| 4,671,256 A | 6/1987 | Lemelson | |
| 5,065,418 A | 11/1991 | Bermbach et al. | |

(Continued)

OTHER PUBLICATIONS

S. Ogorodnikov, V. Petrunin, 'Processing of interlaced images in 4-10 MeV dual energy customs system for material recognition', Physical Review Special Topics—Accelerators and Beams, 2002, vol. 5, The American Physical Society, College Park, MD.

(Continued)

*Primary Examiner*—Edward J. Glick
*Assistant Examiner*—Irakli Kiknadze
(74) *Attorney, Agent, or Firm*—Brandon N. Sklar; Kaye Scholer LLP

(57) ABSTRACT

In one embodiment, a method of examining contents of an object is disclosed comprising scanning an object at first and second radiation energies, detecting radiation at the first and second energies, and calculating a function of the radiation detected at the first and second energies, for corresponding pixels. A pixel is a projection of radiation through the object onto the detector. The first functions of a plurality of pixels are grouped and a second function of the group is analyzed to determine whether the object at least potentially contains material having an atomic number greater than the predetermined atomic number. The second function may be compared to a third function, which may be a threshold having a value based, at least in part, on material having a predetermined atomic number. Systems are also disclosed.

53 Claims, 21 Drawing Sheets

U.S. PATENT DOCUMENTS

| | | |
|---|---|---|
| 5,098,640 A | 3/1992 | Gozani et al. |
| 5,319,547 A | 6/1994 | Krug et al. |
| 5,410,156 A | 4/1995 | Miller |
| 5,490,218 A | 2/1996 | Krug et al. |
| 5,495,106 A | 2/1996 | Mastny |
| 5,524,133 A | 6/1996 | Neale et al. |
| 5,557,108 A | 9/1996 | Tumer |
| 5,600,303 A | 2/1997 | Husseiny et al. |
| 5,600,700 A | 2/1997 | Krug et al. |
| 5,611,502 A | 3/1997 | Edlin et al. |
| 5,682,411 A | 10/1997 | Rushbrooke et al. |
| 5,692,028 A | 11/1997 | Geus et al. |
| 5,696,806 A | 12/1997 | Grodzins et al. |
| 5,729,582 A | 3/1998 | Ham et al. |
| 5,838,758 A * | 11/1998 | Krug et al. .................... 378/53 |
| 5,838,759 A | 11/1998 | Armistead |
| 5,841,832 A | 11/1998 | Mazess et al. |
| 5,905,806 A | 5/1999 | Eberhard et al. |
| 5,917,880 A | 6/1999 | Bjorkholm |
| 5,930,314 A | 7/1999 | Lanza |
| 6,018,562 A | 1/2000 | Willson |
| 6,078,642 A | 6/2000 | Simanovsky et al. |
| 6,088,423 A * | 7/2000 | Krug et al. .................... 378/57 |
| 6,151,381 A | 11/2000 | Grodzins et al. |
| 6,195,444 B1 | 2/2001 | Simanovsky et al. |
| 6,236,709 B1 | 5/2001 | Perry et al. |
| 6,301,326 B2 | 10/2001 | Bjorkholm et al. |
| 6,347,132 B1 | 2/2002 | Annis |
| 6,366,021 B1 | 4/2002 | Meddaugh et al. |
| 6,411,674 B1 | 6/2002 | Oikawa |
| 6,438,201 B1 | 8/2002 | Mazess et al. |
| 6,567,496 B1 | 5/2003 | Sychev |
| 6,584,170 B2 | 6/2003 | Aust et al. |
| 6,936,820 B2 | 8/2005 | Peoples |
| 6,944,264 B2 * | 9/2005 | Bijjani et al. .................. 378/57 |
| 7,023,957 B2 | 4/2006 | Bijjani et al. |
| 7,045,788 B2 | 5/2006 | Iwatschenko-Borho et al. |
| 7,103,137 B2 | 9/2006 | Seppi et al. |
| 7,130,371 B2 | 10/2006 | Elyan et al. |
| 2003/0190011 A1 * | 10/2003 | Beneke et al. ................ 378/57 |
| 2004/0256565 A1 | 12/2004 | Adams et al. |

OTHER PUBLICATIONS

Paul Bjorkholm, Dual Energy Radiation Scanning Of Objects, U.S. Appl. No. 11/070,030, Filing Date Feb. 28, 2005.

Clayton et al., Object Examination By Delayed Neutrons, U.S. Appl. No. 11/070,032, Filing Date Feb. 28, 2005.

* cited by examiner

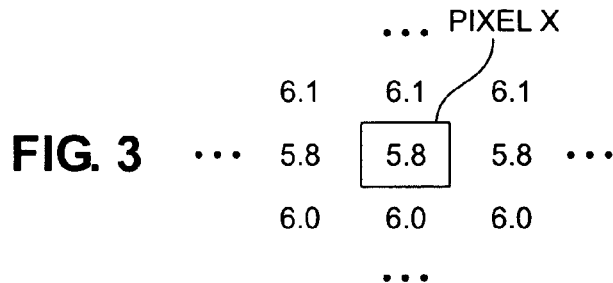
FIG. 3
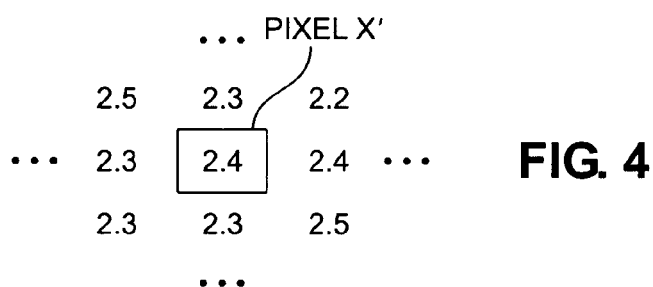
FIG. 4
FIG. 5

DUAL ENERGY RADIATION SCANNING OF CONTENTS OF AN OBJECT

RELATED APPLICATIONS

The present application claims the benefit of Provisional Patent Application No. 60/549,093, filed on Mar. 1, 2004 and Provisional Patent Application No. 60/568,541, filed on May 5, 2004, which are assigned to the assignee of the present invention and are incorporated by reference herein.

FIELD OF THE INVENTION

Radiation scanning of objects, including large objects such as cargo containers, to identify contraband.

BACKGROUND OF THE INVENTION

Radiation is commonly used in the non-invasive inspection of contents of objects, such as luggage, bags, briefcases, cargo containers, and the like, to identify hidden contraband at airports, seaports, and public buildings, for example. The contraband may include hidden guns, knives, explosive devices, illegal drugs, and weapons of mass destruction, such as a nuclear or a "dirty" radioactive bomb, for example. One common inspection system is a line scanner, where the object to be inspected is passed between a stationary source of radiation, such as X-ray radiation, and a stationary detector. The radiation is collimated into a fan beam or a pencil beam. Radiation transmitted through the object is attenuated to varying degrees by the contents. The attenuation of the radiation is a function of the density of the materials through which the radiation beam passes. The transmitted radiation is detected and measured. Radiographic images of the contents of the object may be generated for inspection. The images show the shape, size and varying densities of the contents.

The stationary source of radiation used in a common inspection system is typically a source of X-ray radiation of about 160 KeV to about 450 KeV. The X-ray source may be a source of Bremsstrahlung radiation, for example. The X-ray source in this energy range may be an X-ray tube. X-ray radiation of 450 KeV will not completely penetrate large objects such as cargo containers. Standard cargo containers are typically 20–50 feet long (6.1–15.2 meters), 8 feet high (2.4 meters) and 6–9 feet wide (1.8–2.7 meters). Air cargo containers, which are used to contain a plurality of pieces of luggage or other cargo to be stored in the body of an airplane, may range in size (length, height, width) from about 35×21×21 inches (0.89×0.53×0.53 meters) up to about 240×118×96 inches (6.1×3.0×2.4 meters). Large collections of objects, such as many pieces of luggage, may also be supported on a pallet. Pallets, which may have supporting side walls, may be of comparable sizes as cargo containers and use of the term "cargo conveyance" encompasses cargo containers and pallets.

While the smuggling of guns, explosives and other contraband onto planes in carry-on bags and in luggage has been a well known, ongoing concern, a less publicized but also serious threat is the smuggling of contraband across borders and by boat in large cargo conveyances. Only 2%–10% of the 17 million cargo containers brought to the United States by boat are inspected. "Checkpoint Terror", U.S. News and World Report, Feb. 11, 2002, p. 52.

Atomic bombs and "dirty bombs," which use a conventional explosion to disperse radioactive material over a wide territory, are examples of nuclear devices that may be smuggled in cargo conveyances and smaller objects. Radioactive, fissionable, fissile, and fertile materials that may be used to manufacture atomic devices, may also be similarly smuggled in such objects. Fissile materials, such as uranium-235, uranium-233, and plutonium-239, may undergo fission by the capture of a slow (thermal) neutron. Fissionable materials include fissile materials, and materials that may undergo fission by capture of fast neutrons, such as uranium-238. Fertile materials may be converted into fissile materials by the capture of a slow (thermal) neutron. Uranium-238, for example, may be converted into plutonium-239. Thorium-232, for example, may be converted into uranium-233. Fissionable, fissile, and fertile material are referred to herein as "nuclear material."

Identification of nuclear devices, nuclear materials, and radioactive materials (that may not be nuclear materials), by manual inspection of the contents of an object, such as a cargo conveyance, is too slow for regular use. Identification of radioactive materials and nuclear devices by passive inspection systems, such as a radiation detector, while faster, is difficult. For example, the radiation detector may be positioned along a path of an object. Since nuclear materials are typically dense, however, they absorb most of the photons they emit. Shielding material, such as iron, lead, tungsten, or palladium may also be used to block the escape of radiation, preventing its detection. In addition, certain fissile materials, such as uranium-233, uranium-235, and plutonium-239 while radioactive, have exceedingly long half-lives (on the order of $10^4$–$10^8$ years). The count rate from spontaneous decays for such material is so low, that passive detection is not reliable. Also, a relatively small amount of radioactive material may be located within a large cargo conveyance. It is also difficult to distinguish nuclear devices and nuclear materials from other dense items that may be contained within the object by standard X-ray scanning.

The information that may be derived about the material composition of the contents of objects by X-ray scanning may be enhanced by the use of radiation beams with energy spectra having two different energy endpoints (peak energies) that interact differently with the contents of the object. The interaction is material dependent. For example, two X-ray beams with energy spectra may be provided by X-ray sources with accelerating potentials of 6 MV and 9 MV or higher, which generate X-ray radiation beams with peak energies of 6 MeV and 9 MeV, respectively. For an X-ray beam having a peak energy of 6 MeV, the X-ray radiation will be attenuated mainly by Compton scattering. There is not much pair production over most of that spectrum. For an X-ray beam having a peak energy of 9 MeV or higher, more pair production is induced. Compton scattering also takes place. A ratio of the transmitted radiation detected at two energy endpoints may be indicative of the atomic numbers of the material through which the radiation beam passes. Although pair production starts at 1.022 MeV, Compton scattering predominates until higher peak energies are reached.

U.S. Pat. No. 5,524,133, for example, discloses scanning systems for large objects such as freight in a container or on a vehicle. In one embodiment, two stationary sources of X-ray radiation are provided, each emitting a beam that is collimated into a fan beam. The sources facing adjacent sides of the freight and the fan beams are perpendicular to each other. A stationary detector array is located opposite each source, on opposite sides of the freight, to receive radiation transmitted through the freight. In addition, X-ray radiation of two different energies are emitted by each source. One energy is significantly higher than the other. For example, energies of 1 MeV and 5 or 6 MeV may be used. A ratio of the mean number of X-rays detected at each energy endpoint by the detector array as whole for each slice or by the individual detectors of the array is determined and compared to a look up table to identify a mean atomic number corresponding to the ratio. The material content of the freight is thereby determined.

A further complication with X-ray scanning is that measurements of radiation after interaction with the object under inspection are statistical. The accuracy of a measurement of X-ray radiation transmitted through an object is limited by the number of photons used to make the measurement, as well as intrinsic system noise, for example. Repeated measurements of the same quantity typically yield a cluster of measurement values around a mean value. A plot of the cluster of measurements typically forms a "normal distribution" curve. The dispersion of the individual measurements (the width of the normal distribution curve) is characterized by a standard deviation. Using Poisson statistics in X-ray scanning with a monochromatic X-ray beam, the percentage error of the measurements is one (1) divided by the square root of the number of photons detected, exclusive of system noise. As more photons are detected, the standard deviation decreases and the accuracy of measurement increases. While the number of photons detected may be increased by increasing the scanning time, it is generally not acceptable to slow the throughput rate of a typical X-ray scanning system. For example, it is unacceptable in the current marketplace to significantly delay the passage of cargo conveyances through ports or borders, or to delay the screening of passenger's bags and luggage at airports.

The accuracy of a scanning system seeking to identify a material, such as uranium, for example, may be characterized by its "sensitivity" and its "specificity". Sensitivity is the probability that the presence of uranium in a cargo conveyance will be identified. A system with high sensitivity will identify more true positives (correct identification of the presence of uranium) and fewer false negatives (missed detection of uranium) than a system with low sensitivity. However, increased sensitivity may result in an increase in the number of false positives, which may not be acceptable. Specificity, which is a statistical measure of accuracy, is the probability that the scanning system will properly identify the absence of uranium in a cargo conveyance, for example. A system with high specificity will identify fewer false positives (identification of uranium in a cargo conveyance when it is not present), than a system with low specificity.

The collection of insufficient photons may result in measurement distributions with large standard deviations. The distributions for materials of interest, such as uranium, may therefore overlap the distributions of other, non-threatening materials. Therefore, it may not be clear whether a particular measurement is indicative of a material of interest or not, resulting in false positives. Practical, efficient, and non-intrusive methods and systems for detection of nuclear materials hidden inside cargo conveyances and other objects, with higher accuracy, are still needed.

SUMMARY OF THE INVENTION

Fissionable, fissile, and fertile materials ("nuclear materials") have high atomic numbers (Z). For example, uranium has an atomic number ("Z") of 92 and plutonium has an atomic number of 94. Special Nuclear Material ("SNMs"), which more readily undergo fission than other fissile materials, are defined by the U.S. Nuclear Regulatory Commission to include plutonium, uranium-233, and uranium enriched in the isotopes of uranium-233 or -235. Radioactive materials, certain of which may have lower atomic numbers than nuclear materials (cobalt-60, for example, has an atomic number of 27), are typically shielded by high atomic number materials, such as lead (Z=82), tungsten (Z=74), and palladium (Z=46). Iron, which is a main material in a majority of industrial goods shipped in cargo conveyances, in contrast, has an atomic number of 26. Agricultural goods, which may also be shipped in cargo conveyances, have even lower atomic numbers. Agricultural goods are predominantly composed of carbon (Z=6), nitrogen (Z=7), and water ($H_2O$, H (Z=1); O (Z=8)), which have even lower atomic numbers. Embodiments of the invention examine contents of objects for the presence of high atomic number materials that may be indicative of the presence of nuclear materials. Objects themselves and objects buried underground may be examined, as well.

In accordance with embodiments of the invention, the contents of an object is examined by scanning the object with radiation beams having different energies, such as different energy endpoints, calculating a function of the radiation detected at the two energies, and determining whether the object comprises a material having an atomic number greater than a predetermined atomic number based, at least in part, on the function. The object may be a cargo conveyance and both energy endpoints may be greater than 1 MeV, for example. The energy endpoints may be 9 MeV and 5 MeV, for example. The function may be a ratio between the radiation detected at the two energy endpoints, for example. Such a ratio is referred to herein as a transmission ratio ("TR"). Material having an atomic number greater than the predetermined atomic number is referred to as high atomic number material ("HANM"). The first function may be compared to a second function that is based, at least in part, on the predetermined atomic number, to make the determination. The second function may be a threshold, for example. The threshold may be based, at least in parts on a ratio (also a TR) derived from scanning a test material having the predetermined atomic number, at the same two energy endpoints, for example. The threshold may be further adjusted by a predetermined integral or non-integral number of standard deviations. Varying the number of standard deviations will affect the sensitivity and specificity of the system, typically in opposite directions. For example, increasing the number of standard deviations may improve the specificity, decreasing the number of false positives, but it may also decrease the sensitivity, decreasing the detection of true positives. Specificity and sensitivity need to be balanced in a particular application.

A projection of a portion of the radiation beam transmitted through a particular portion of the object, onto a surface, such as a detector, is referred to as a "pixel." Functions may be calculated between radiation detected at each energy, for corresponding pixels. Corresponding pixels preferably overlap by at least one-half, but that is not required. The projection of the corresponding pixels onto the surface is referred to as "resultant" pixels or just pixels.

Resultant pixels meeting the test criterion are at least potentially indicative of an HANM in the associated region of the object. To improve the specificity and sensitivity of the conclusion that HANM is present, embodiments of the invention analyze different types of resultant pixel groupings, in different ways. A grouping may be formed about each suspect resultant pixel (a resultant pixel that meets the test criterion), or a plurality of groupings may be formed to encompass all pixels in an array. Multiple tests may be conducted.

In accordance with an embodiment of the invention, a method of examining contents of an object is disclosed comprising scanning first portions of the object with a first radiation beam at a first energy and detecting first radiation after interaction of the first radiation beam with the first portions. The method further comprises scanning second portions of the object with a second radiation beam and detecting second radiation after interaction of the second radiation beam with the second portions. The method continues by calculating first functions of the radiation detected at the first and second energies for corresponding first and second pixels and grouping first functions of a plurality of corresponding pixels into at least one group. The method further comprises calculating a second function based on the first functions of at least certain of the plurality of pixels in the at least one group and determining whether the object at least potentially contains material having a high atomic number greater than a predetermined atomic number, based, at least in part, on the second function of the at least one group.

In accordance with a related embodiment, a method of examining contents of an object is disclosed comprising scanning an object with first and second radiation beams at first and second energies, as above. The method further comprises detecting first and second radiation transmitted through the object at the first and second energies. The method then continues by calculating ratios between functions of the first radiation and functions of the second radiation for each of a plurality of pairs of corresponding first and second pixels and storing the respective ratios in an array comprising rows and columns corresponding to the resultant pixels. The method further comprises comparing the respective ratios with a threshold that is a function of a predetermined atomic number and selecting at least one examination window comprising a plurality of rows and columns of respective ratios. The method continues by determining whether the object at least potentially contains material having an atomic number greater than the predetermined atomic number based, at least in part, on whether a predetermined number of respective ratios in each of the at least one examination windows meeting criterion with respect to the respective ratios and the threshold, is greater than a predetermined number.

In accordance with another related embodiment, a method of examining contents of an object is disclosed wherein an object is also scanned, radiation is detected, ratios are calculated, and compared to a threshold, as above. The method continues by grouping a plurality of resultant pixels, calculating a function of the ratios of the grouping, and comparing the function with the threshold. The method further comprises determining whether the object at least potentially contains material having an atomic number greater than the predetermined atomic number based, at least in part, on the comparison of the function of the ratios of the grouping to the threshold.

In accordance with another related embodiment, a system for examining contents of object is disclosed comprising at least one radiation source to scan at least a portion of an object with first and second radiation beams at first and second radiation energies. At least one detector is positioned to detect radiation at the first and second radiation energies after interaction with the object. At least one processor is coupled to the detector. The at least one processor is programmed to calculate first functions of the radiation detected at the first and second energies, for corresponding first and second pixels, group first functions of a plurality of corresponding pixels into at least one group, and calculate a second function of the first functions of the plurality of pixels in the at least one group. The at least one processor is further programmed to determine whether the object at least potentially contains high atomic number material having an atomic number greater than a predetermined atomic number based, at least in part, on the second function of the at least one group.

The term "radiation energy" refers to an energy characteristic of the radiation beam. The characteristic may be the energy endpoint or peak energy of the beam, for example. The radiation energy may also refer to an average or nominal value of the energy of the beam. Other characterizations of the energy of the beam may be used, as well.

BRIEF DESCRIPTION OF THE DRAWINGS

FIG. 3 is an example of an array of values of X-ray radiation of 9 MeV transmitted through a portion of a cargo conveyance, at a plurality of pixels;

FIG. 4 is an example of an array of values of X-ray radiation of 5 MeV transmitted through the portion of the cargo conveyance of FIG. 6, at a plurality of pixels;

FIG. 5 is an example of an array of transmission ratios ("TRs") for a group of resultant pixels based on the X-ray radiation measured in FIGS. 3 and 4, in accordance with an embodiment of the invention;

DESCRIPTION OF THE PREFERRED EMBODIMENTS

Figure 1A:
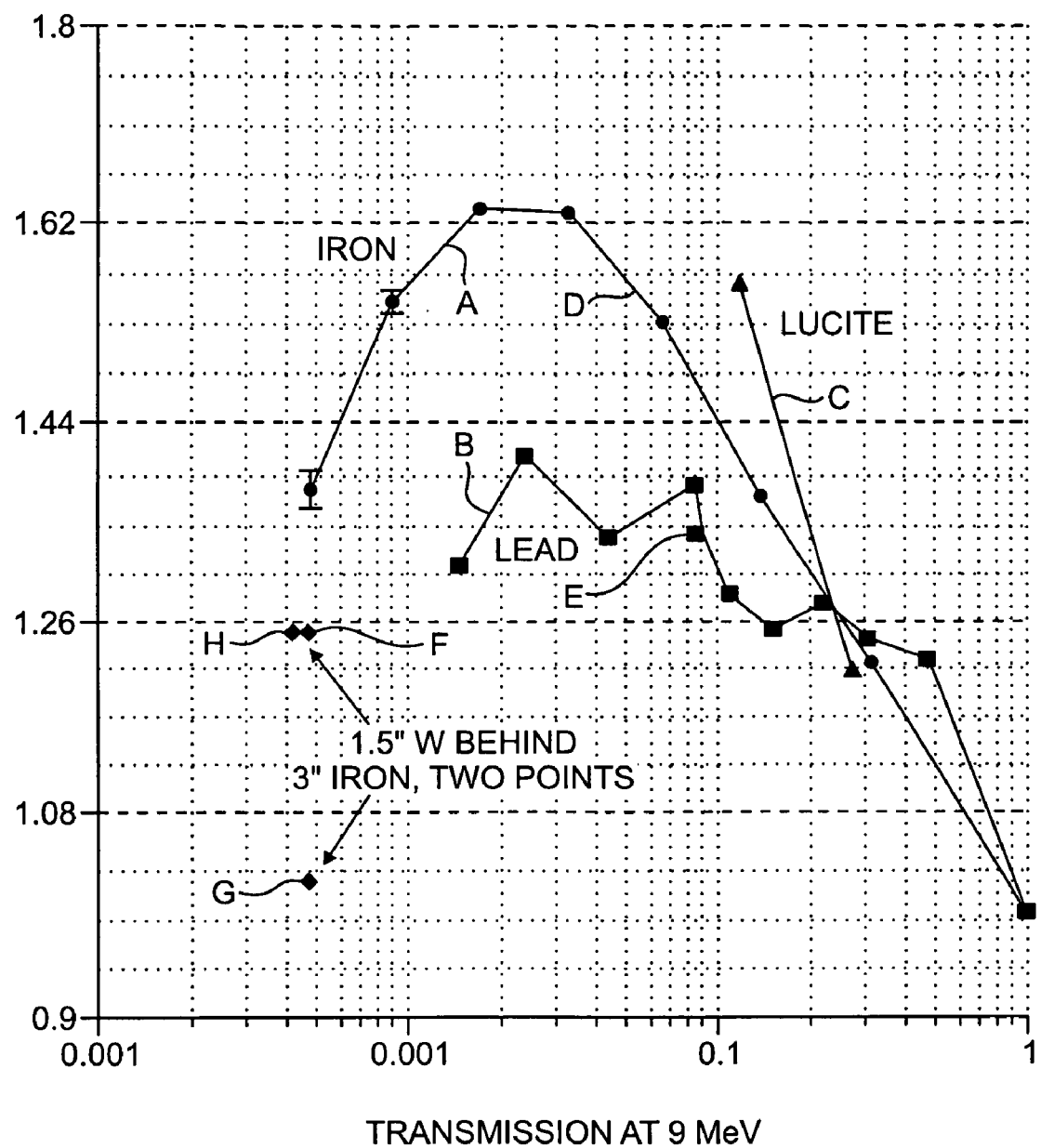
FIG. 1a is a graph of measurements of transmitted radiation at 9 MeV and 5 MeV as a function of transmitted radiation at 9 MeV, for a variety of materials.

In accordance with embodiments of the invention, a function of the transmission or attenuation of radiation through an object at two different energies is used to classify the object or items or regions within the object as a high atomic number material ("HANM"), which may be a nuclear material or shielding for such material. The function may be a ratio. The ratio or other such function may be compared to the same function of transmission or attenuation of radiation at the same two energies through a test material of known atomic number. Material may be classified as HANM if it has a higher atomic number than the test material. The test material may be any material with an atomic number less than the atomic number of a material of concern. The test material may be iron, for example. The object may be a cargo conveyance, for example. Also, in accordance with embodiments of the invention, the determination may be made to a desired degree of statistical confidence.

Iron has an atomic number ("Z") of 26. Since typical items in a cargo conveyance comprise iron and other materials with atomic numbers less than iron, the presence of any material having an atomic number greater than iron is suspicious. It is therefore sufficient to screen for HANMs, without identifying the particular material (although that is an option). While some HANM may not be nuclear materials, non-nuclear HANMs, such as lead (Pb, Z=82), tungsten (W, Z=74), and bismuth (Bi, Z=83) may be used to shield nuclear materials, and are, therefore, also suspect materials. The presence of legitimate HANMs in cargo conveyances and the like is rare, and when they are present, they should be identified on a manifest for the cargo conveyance. Silver (Ag, Z=47), for example, has medical, industrial, and photographic uses. If silver is being shipped for such legitimate uses, it should be identified on the manifest. In addition, nuclear material may be distinguished from other HANM by their transmissions and shapes in an image. Checking the manifest and visually inspecting an X-ray image of the cargo conveyance may thereby avoid identification of the HANM as a nuclear material, decreasing the incidence of false positives.

To demonstrate that ratios of transmission through different materials at different energies enables classification of materials as HANM, samples of iron, lead, lucite, and tungsten were scanned with radiation beams having nominal energies of 9 MeV (measured half value layer ("HVL") 1.16 inches, 2.95 cm) and 5 MeV (HVL 1.04 inches, 2.64 cm). The radiation beam was provided by an M9 Linatron® linear accelerator, available from Varian Medical Systems, Inc., Palo Alto, Calif., that was set to run at 8.5 MeV and 4.5 MeV. The M9 may be switched from one energy endpoint to another energy endpoint. Each sample was scanned at one energy end point, data was collected, and then the sample was scanned at the second energy endpoint and data was collected. Radiation transmitted through each sample was detected by a Paxscan® 4030 gadolinium oxide (GdO) scintillator about two meters from the source, positioned along a central axis of the source. The electronics portion of the detector was covered by lead. For the 8.5 MeV data acquisition, the detector was run at 300 pulses per second ("pps") and the detector was run at 1.5 frames per second ("fps"). For the 4.5 MeV data acquisition, the source was run at 200 pps and the detector was run at 3 fps. The images were summed over 128 frames.

Samples of the iron, lead, and lucite of varying thicknesses were individually placed between the source and the detector. The different thicknesses resulted in different amounts of transmission. For each sample, two images were acquired and stored in .viv format. Each image was normalized to correct for detector non-uniformities, and stored. In addition, samples of different materials were placed next to each other. For example, tungsten and iron were separately placed next to lead. Also, samples of multiple materials were placed one behind another, along the direction of the beam. For example, tungsten and lead were separately placed behind iron.

Each image was processed by ImageJ, image processing and analysis in Java, a freeware program available from the National Institutes of Health at http://rsb.info.nih.gov/ij/, for example. Other image processing software known in the art could be used, as well. A histogram of a region of interest of an image was obtained at a fixed location in each image and the mean and standard deviation of the data collected from the region of interest were recorded. In some cases, when two different materials were placed next to each other, regions of interest had to be chosen by hand, instead of by a macro. The corresponding locations of the sample scanned at both energies were not, therefore, exactly the same. A location indicator in ImageJ enabled the location to be at least very close.

The energy transmission for each image was computed by dividing a histogram mean of the image by a histogram mean of an image at the same energy without the sample present, to normalize the image. A ratio of the energy transmissions at 8.5 MeV to 4.5 MeV were then calculated and recorded. The transmission at 8.5 MeV was also recorded.

The results are shown in FIG. 1a, which is a graph of the ratio of the transmission of a radiation beam having a nominal energy of 9 MeV to the transmission of a radiation beam having a nominal energy of 4.5 MeV, along the Y axis, versus the transmission at 8.5 MeV, along the X axis. The X axis is semi-logarithmic. Curve A is a guide to the eye connecting calculated ratios at different transmissions, which correspond to different thicknesses of the sample, for iron. Curve B connects calculated ratios at different transmissions for lead. Curve C connects calculated ratios at different transmissions for lucite. Point D shows the ratio for iron next to tungsten. Point E shows the ratio for lead next to iron. Point F shows the ratio for transmission through 1.5 inches (38.1 mm) of tungsten behind 3 inches (76.2 mm) of iron. Point G shows the ratio for 1.5 inches (38.1 mm) of tungsten behind 3 inches (76.2 mm) of iron in a different image. Point H shows the ratio for 3 inches (76.2 mm) of lead behind 3 inches of iron (76.2 mm).

The curves and points in FIG. 1a show good separation between materials at low transmission (high attenuation). Iron, lead, and lucite may be clearly distinguished at transmissions of about 0.1 and less, as can tungsten and lead behind iron. In addition, the position of the curves with respect to each other shows that the ratios for materials decrease as the atomic number increases, in this example. Materials may therefore be classified as HANM based on the ratios for each material and comparison to a respective ratio to a ratio of iron, for example. It is noted that the curves converge as complete transmission (X=1) is approached. Separation of could probably be determined at higher transmissions (less attenuations), as well, if a greater number of photons are detected and there is less scatter, in an optimized system, for example.

Figure 1B:
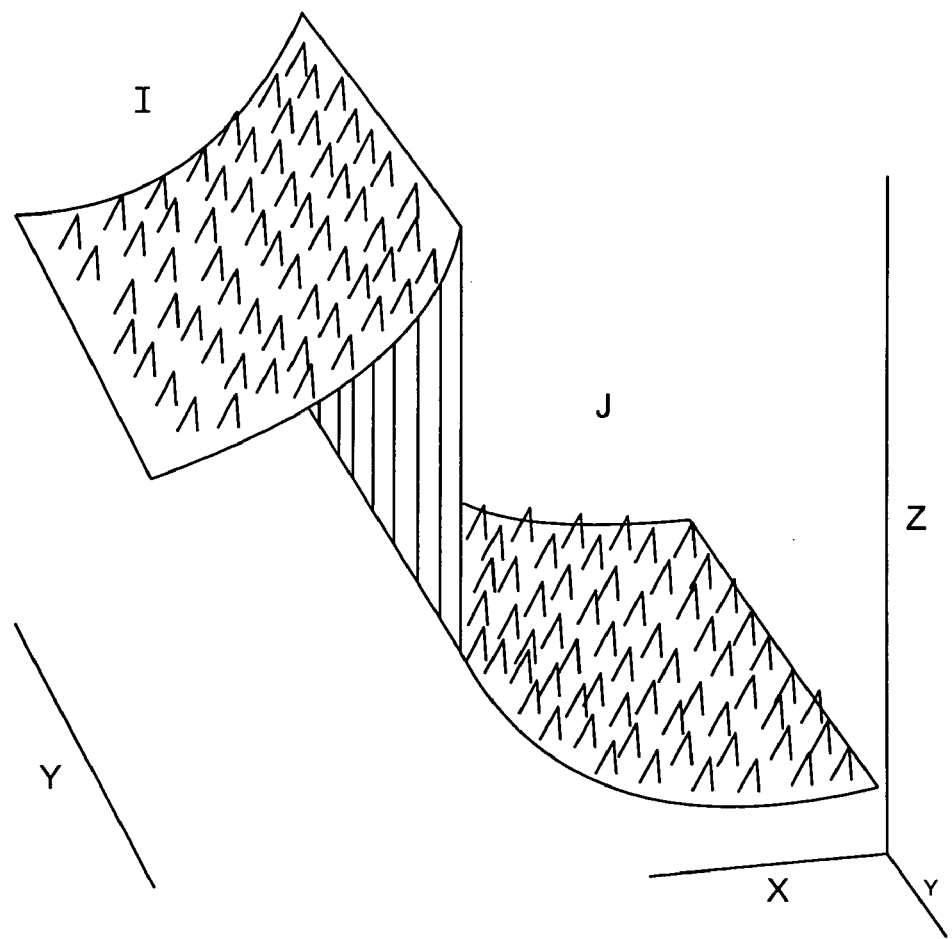
FIG. 1b shows a surface plot of ratios of transmitted radiation at 9 MeV to 5 MeV, through a piece of iron adjacent to a piece of lead.

FIG. 1b is a surface plot of a ratio image between transmission at 8.5 MeV and transmission at 4.5 MeV through 3 inches (76.2 mm) of steel (iron) adjacent to 1.5 inches (38.1 mm) of lead. Different thicknesses are used so that the transmission is the same through both materials. Portion I of the image is that of steel (iron) and portion J of the image is that of lead. The steel (iron) and lead have about the same energy transmission at 8.5 MeV, as measured by the detector. The ratios are significantly different. The roughness in each surface is due to statistical variations in the ratio measurement. The two materials may be readily distinguished because their ratios are separated by many standard deviations. Where the transmission is lower, the standard deviations will be larger, the ratios will be closer together, and more sophisticated statistical analysis would be required.

Figure 1C:
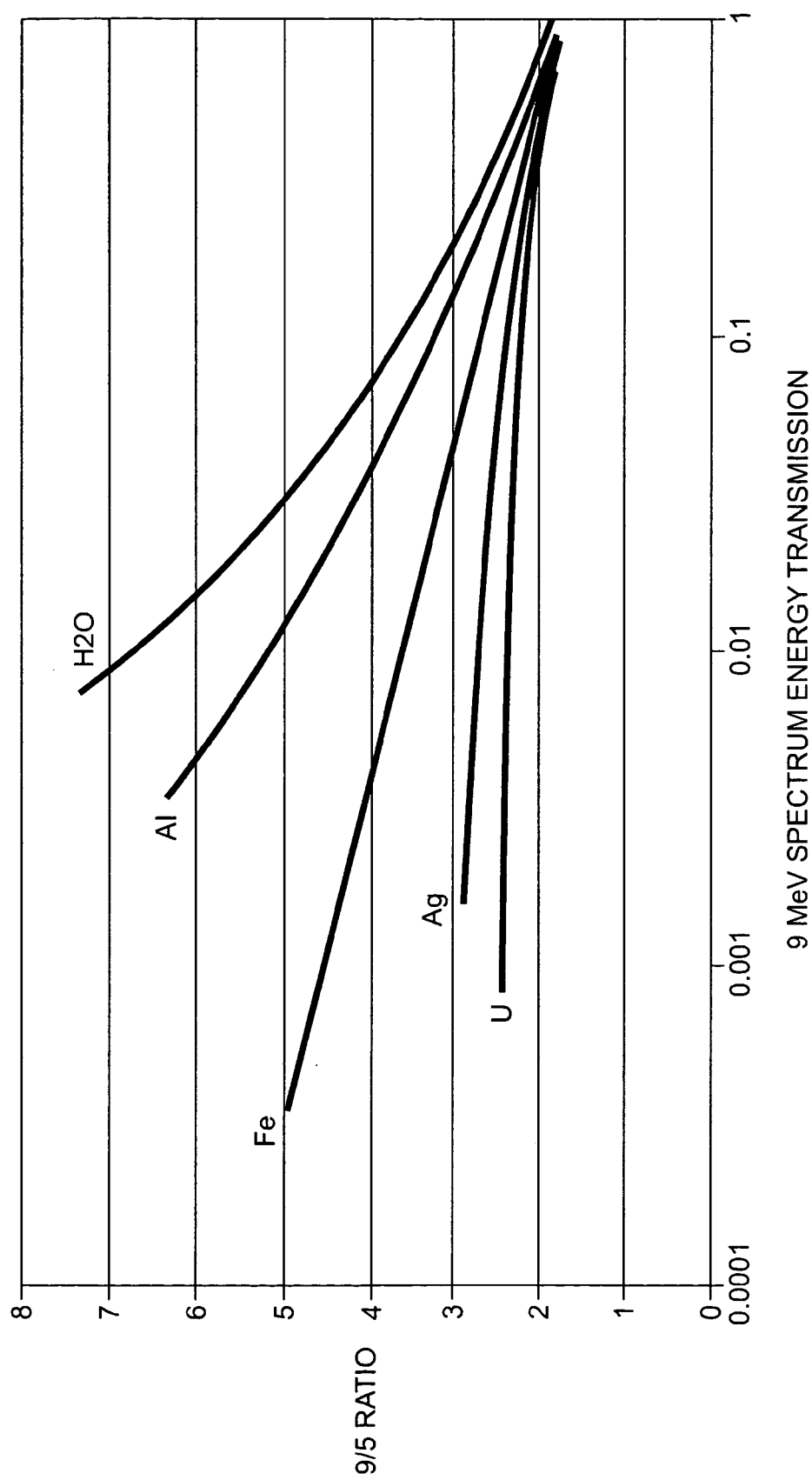
FIG. 1c shows five curves representative of ratios of simulated measurements of transmitted radiation at 9 MeV and 5 MeV as a function of transmitted radiation at 9 MeV, through identified materials.

In the experiment described above, the source and the detector were close together, requiring a wide radiation beam, which decreases the uniformity of incident radiation. In addition, scatter was not reduced and the detector efficiency was low. FIG. 1c shows five curves depicting simulated ratios of radiation transmitted through five (5) different materials at 9 MeV to transmitted energy at 5. Me V, as a function of the energy transmitted at 9 MeV, based on a simulation without these problems. The detector comprises 30 mm cadmium tungstiate ($CdWO_4$). In the simulation, scatter was reduced, the source and the detector were further apart and (about 13 meters) as compared to the actual test, above. The materials were water ($H_2O$), aluminum, iron, uranium, and gold, as indicated. The curves are smoother than in the test above, and converge as transmission at 9 MeV increases: As above, at high attenuation of the incident radiation (low transmission), there is significant separation among the different materials. The separation, which increases as transmission decreases (attenuation increases), shows a dependence on atomic number. In addition, the ratio decreases as the atomic number increases, in this example. If the ratio was calculated by dividing the lower energy by the higher energy, then the ratio would increase as the atomic number increases.

Without being limited to any particular theory, it is believed that the relationship between the ratio and the atomic number results from the differential effects of Compton Scattering and pair production at different energies. With low atomic number materials (such as aluminum (Z=13) and water ($H_2O$, H (Z=1), O (Z=8))), Compton scattering is the dominant mechanism at high energies, such as 9 MeV. Compton scattering causes the low atomic number materials to scatter lower energy photons, such as 5 MeV photons, at a higher rate than they scatter higher energy photons, such as 9 MeV photons, which increases the ratio of transmitted radiation for low atomic number materials. For higher atomic number materials, such as silver (Z=47) and uranium (Z=92), pair production causes removal of the high energy photons, thus reducing the ratio. In addition, the variation of the ratio is less sensitive to changes in energy transmission, resulting in a nearly flat curve as energy transmission increases.

In FIGS. 1a and 1c, if iron (Fe, Z=26), which has the highest atomic number among materials commonly found in cargo conveyances, is used as a test material, calculated ratios less than the ratio of iron is indicative of the presence of a material having an atomic number greater than iron. As discussed above, typical items in a cargo conveyance comprise iron and other materials with atomic numbers less than iron. The presence of any material with an atomic number greater than iron is, therefore, suspicious.

FIGS. 1a and 1c also show that as the energy transmission increases (because the materials are thinner), the difference between'the ratios for different materials decreases. While FIGS. 1a and 1c show greater differences between the ratios for different elements and substances as energy transmission decreases (for thicker objects), it is noted that as the energy transmission gets smaller, fewer photons per pixel may be detected. This may increase the error margin of the measured ratio, decreasing the accuracy with which materials may be differentiated. Embodiments of the present invention account for the noisy data, statistically.

In examples of embodiments of the present invention, the relationship between the ratio of transmission or attenuation of radiation through a material at two different energies and the atomic number of the material is used to determine whether an object at least potentially contains materials having atomic numbers greater than a predetermined atomic number, which is considered to be a high atomic number material ("HANM"). The predetermined atomic number is selected so that the HANM may be a nuclear material or shielding for a nuclear material.

In one example, an object is scanned with at least two different X-ray energy distributions or spectra having different maximum energy levels, which is also referred to as endpoints or peak energies. Examples of energy distributions that may be used include 5 MeV and 9 MeV, 1 MeV and 9 MeV, and 5 MeV and 15 MeV. The radiation transmitted through the object at the two different energy endpoints is measured by detector elements of a detector array. Radiation may also be detected at each energy end point after being transmitted through the air just before an object enters the respective radiation beam, for example, for use in normalization. Normalization for air transmission is optional. Each detector element receives radiation along a beam path through portions of the object, from the X-ray source to a detector element. A projection of the radiation transmitted along each beam path, onto a surface, is referred to as a "pixel." The surface may correspond to all or a part of a receiving surface of the detector array, which may be flat or curved, for example, as is known in the art. Each pixel may correspond to one or more detector elements of the detector array. If an image is generated, which is an option but is not required in embodiments of the present invention, the pixels may correspond to pixels of the image.

A function of the detected radiation at the two different energy endpoints for corresponding portions or pixels is calculated. "Corresponding" portions or pixels result from the same or substantially the same beam path through the object. Since the object is typically being moved across a radiation beam during scanning, the object may be moved a slight distance between scanning at the first and second energy endpoints. Corresponding pixels may not, therefore, be derived from exactly the same beam path through the cargo conveyance. Preferably pixels are considered to be "corresponding" if their respective beam paths through the cargo conveyance overlap by at least one-half, although that is not required. For example, the pixels may overlap by less than half. It will be apparent to those skilled in the art that in certain cases, such as if less sensitivity and specificity may be tolerated, corresponding pixels may be proximate to each other (within a few pixels of each other) and need not overlap.

As discussed above, the function may be a ratio between the radiation detected at the higher energy endpoint (such as 9 MeV) and the radiation detected at the lower energy endpoint (such as 5 MeV), or vice versa, for example. Such a ratio is referred to as a transmission ratio ("TR"). To calculate the TR in one example, transmitted radiation detected at the higher energy endpoint is divided by transmitted radiation detected at a lower energy endpoint for a plurality of corresponding pixels. TRs for the corresponding pixels, referred to as "resultant pixels" or just pixels, may be represented as an array or a matrix of numbers (corresponding to the ratios) associated with the positions of respective resultant pixels. Instead of measuring radiation transmission, radiation attenuation may be measured and used in the ratio. Other functions may be used, as well. For example, an asymmetric parameter function may be used, such as a ratio between: 1) the energy detected at a first energy endpoint plus the energy detected at a second energy endpoint, and 2) the energy detected at the first energy endpoint minus the energy detected at the second energy endpoint. In other words, (detected radiation at 9 MeV+detected radiation at 5 MeV)÷(detected radiation at 9 MeV−detected radiation at 5 MeV), or vice-versa.

In embodiments of the invention, the TRs of resultant pixels are compared with a second function based on a test material having the predetermined atomic number (above which materials are considered to be HANM). Potential HANM are identified based, at least in part, on whether the TRs meet criterion with respect to the second function. The second function may be a threshold, for example, and the criterion may be whether the TR is above or below the threshold. The threshold may be determined by calculating an average of the TRs of the transmitted radiations at the same two energy endpoints as is used by the system to scan an object under inspection, for the resultant pixels of the test material. All resultant pixels may be analyzed or a statistically sufficient number of resultant pixels may be analyzed to characterize the test piece. Preferably, the average TR is adjusted by an integral or non-integral number of standard deviations of the TRs, to achieve a desired sensitivity and specificity. It is also preferred to calculate the average TR for different thicknesses of the test piece. Since transmission varies with thickness, particular thresholds may thereby be calculated and used for particular transmissions or range of transmissions detected at each pixel. The transmission at the higher energy endpoint, here 9 MeV, may be used to select the threshold. The transmission at 5 MeV may be used, instead.

Preferably, the test material has an atomic number equal to or greater than known the highest atomic number of acceptable materials. For example, radioactive materials, such as uranium (Z=92) and plutonium (Z=94), are of particular concern because they can undergo self-sustaining fission reactions. The test material, therefore, preferably has an atomic number less than the atomic number of uranium. As mentioned above, lead (Z=82), tungsten (Z=74), and bismuth (Z=83) are also of concern because they may be used to shield radioactive material. More preferably, the test material therefore has an atomic number less than tungsten. It is even more preferred that the test material be iron (Z=26), which is the highest atomic number material commonly found in cargo conveyances and luggage in significant quantities. Copper (Z=29) and nickel (Z=28), which have atomic numbers close to iron, may also be used. If the cargo conveyance or other such object contains agricultural products, which may be determined based on a manifest for the cargo conveyance, for example, then a threshold based on a test piece of a plastic, such as Lucite® or Delrin®, may be used. Iron, copper, nickel or other materials having atomic numbers less than the materials of concern may be used in the analysis of cargo conveyances containing agricultural goods, as well.

The result of the comparison of the TR of the pixels to the threshold is indicative of whether the atomic number of the material in the volume of the object traversed by the radiation beam is above or below that of the material of the test piece. In the case where the TR is calculated by dividing a value of a high energy pixel by a value of a corresponding low energy pixel, if the TR is less than the threshold, then the volumes traversed by the radiation beams resulting in those pixels at least potentially comprise material having a higher atomic number than the material of the test piece and is identified as at least a potential HANM. Materials below that atomic number are classified as non-HANM. In the case where the TR is calculated by dividing the value of a low energy pixel by the value of a corresponding high energy pixel, if the TR is greater than the threshold, then the volumes traversed by the radiation beams resulting in those pixels at least potentially comprises material having a higher atomic number than the material of the test piece and is identified as at least a potential HANM. It is noted that in accordance with these embodiments of the invention, it is not necessary to identify the atomic number of the material, although that is an option, as is known in the art. U.S. Pat. No. 5,524,133, for example, which is discussed above, describes a dual energy technique for identifying a mean atomic number of material based on a ratio of X-ray radiation detected at each energy.

Figure 2:
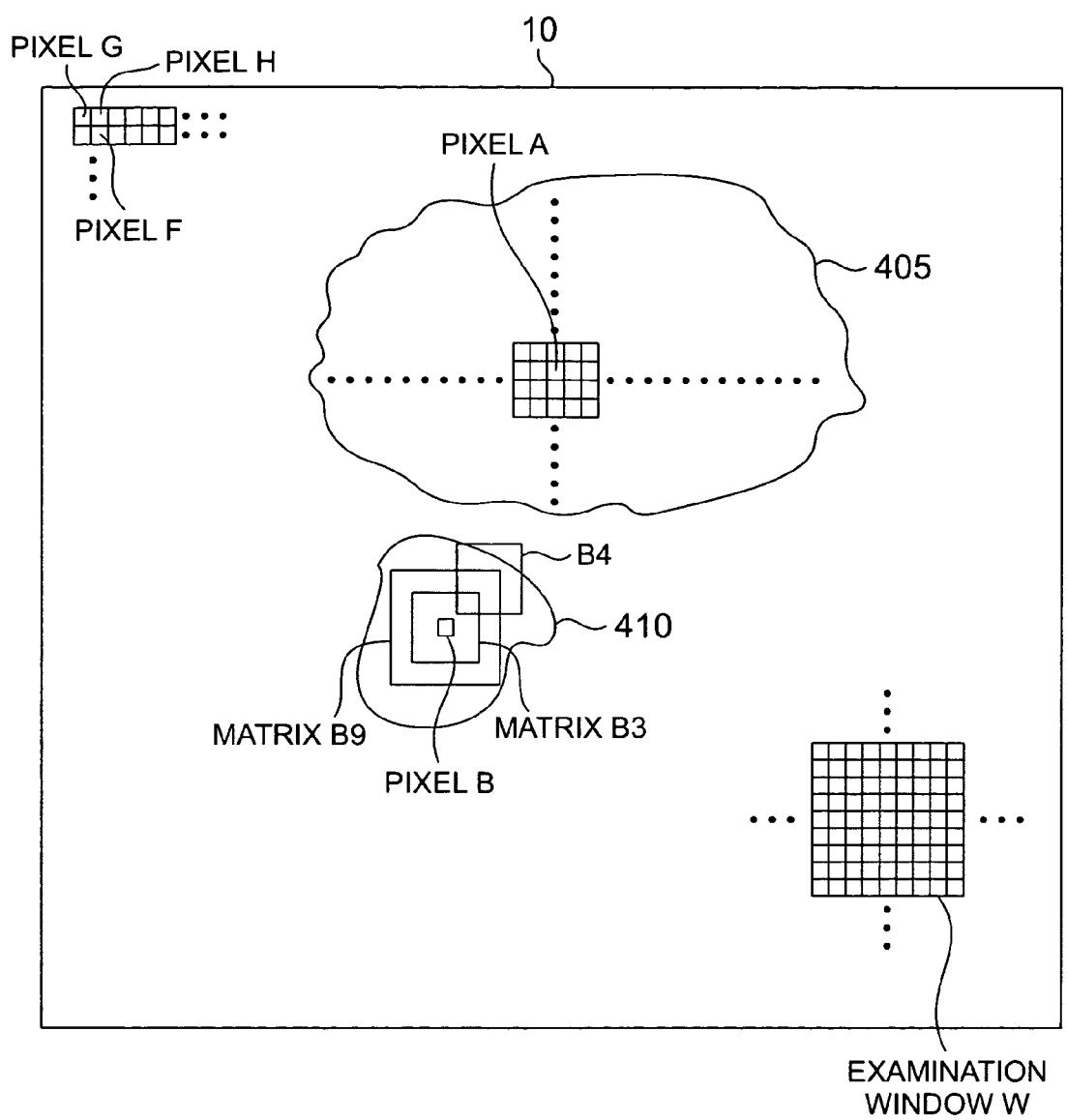
FIG. 2 is a schematic representation of an example of a portion of an X-ray image of a cargo conveyance.

FIG. 2 is an image 10 of a portion of cargo conveyance containing an item 405, an item 410, and selected pixels, including illustrative pixels A, B, F, G, and H. The pixel A lies within the item 405. The pixel B lies within the item 410. An examination window W, discussed in detail below, is also shown. The size of the pixels may depend on the size and/or number of detector elements comprising the detector, imaging integration time, etc. The smallest pixel size may correspond to a single detector element or number of detector elements. In one example, the size of each detector element and each pixel is 0.5 cm×0.5 cm.

If the radiation beam used to scan the cargo conveyance 10 is a vertical fan beam, FIG. 2 is representative of a combination of a plurality of adjacent vertical, one dimensional scanning arrays resulting from scanning the cargo conveyance. If the radiation beam is a cone beam, FIG. 2 is representative of one or more two-dimensional scanning areas resulting from scanning the cargo conveyance 10.

The values of the transmitted radiation detected at these and other pixels are stored as arrays in memory of a scanning system for processing by a processor, such as a computer. FIG. 3 is an example of a portion of an array of values of radiation energy detected at a plurality of pixels for radiation of 9 MeV transmitted through a portion of a cargo conveyance. FIG. 4 is an example of a corresponding array for radiation detected at corresponding pixels for radiation transmitted through the cargo conveyance at 5 MeV through the corresponding portion of a cargo conveyance. For example, at 9 MeV, the normalized transmitted radiation detected at the pixel X is $5.9 \times 10^{-3}$ and at 5 MeV, the transmitted radiation detected at the pixel X' is $2.4 \times 10^{-3}$. Since all measurements of transmitted radiation are of the same order of magnitude ($10^{-3}$), that term is omitted hereafter. FIG. 5 is an example of an array of the calculated TRs for the same portion of the cargo conveyance as FIGS. 3 and 4. The TR of a resultant pixel A resulting from dividing the value of X (5.9) by the value of X' (2.4) yielding a TR of 2.5, is shown. A resultant pixel typically has the same size and shape as the initial pixels. All of these values are hypothetical.

Figure 6A:
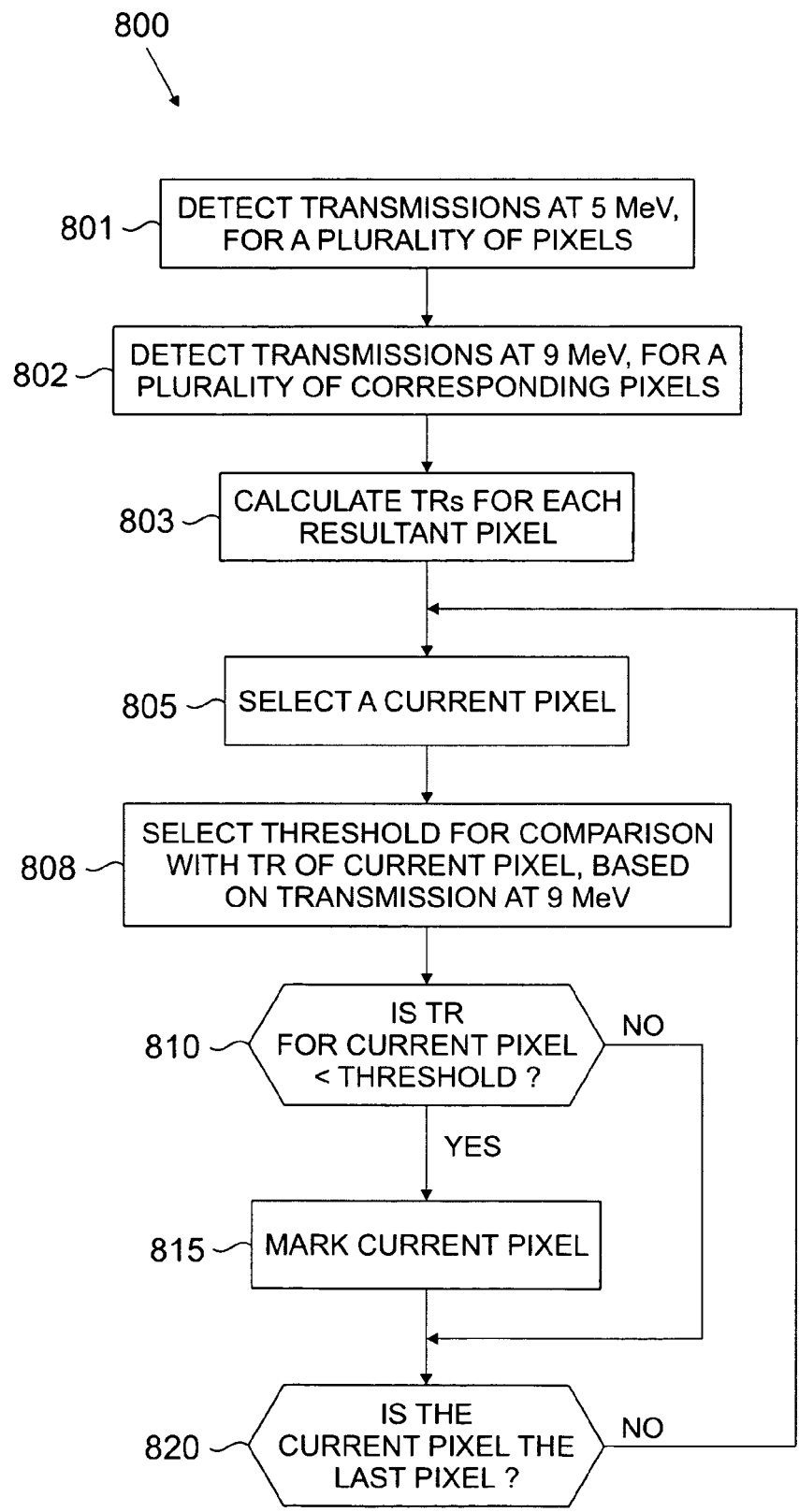
FIG. 6a is a flow chart of an example of a method for adjusting detected radiation through a dense region of an image for background.

FIG. 6a is a flowchart of an example of a method 800 for calculating and analyzing TRs that may be implemented automatically by an X-ray scanning system. In this example, transmission is detected at 5 MeV and at 9 MeV for a plurality of corresponding pixels, in Steps 801 and 802, respectively. In Step 803, the TRs for each resultant pixel are calculated by dividing the measured transmitted radiation at 9 MeV at a pixel by the measured transmitted radiation at 5 MeV at a corresponding pixel, as shown in FIG. 5. A current resultant pixel is then selected for analysis, in Step 805. In this example, the resultant pixel A is selected. A threshold for comparison with the TR of the current pixel is preferably selected based on the detected transmission at one of the energy endpoints, in Step 808. It may be necessary to calculate an applicable threshold based on interpolating stored thresholds, as is discussed further, below. In Step 808, this selection is based on the detected transmission at 9 MeV. It may be based on the detected transmission at 5 MeV, instead. The selected threshold in this example is 4.35.

It is then determined whether the TR of the current resultant pixel A is below the threshold of 4.35, in Step 810. Since 2.5 is less than 4.35, this condition is satisfied. Resultant pixel A may, therefore, be an HANM. The pixel is "marked" as a potential HANM by flagging its place in the array of FIG. 6a, in Step 815. It is then determined whether the resultant pixel. A is the last pixel to be analyzed, in Step 820. Since there are other pixels to be analyzed, the condition is not satisfied and the method returns to Step 805 to select a new pixel for analysis, and the method continues. After the computer has completed analysis of the TRs of all the pixels, the condition in Step 820 becomes true as the current pixel is the last pixel. The processing steps of the method 800 may be conducted by a processor, such as a computer, of the scanning system.

The throughput of a scanning system may be increased by conducting a prescan by known techniques to determine whether the object contains one or more dense regions that warrant further examination. If so, one or more of the tests described herein may be conducted. If not, the object may pass through the system without further examination. The prescan may comprise scanning the object with a radiation beam having one of the energy endpoints. Use of the lower energy endpoint radiation beam is preferred because it is generally more sensitive. The results may be analyzed for radiation attenuation or transmission indicative of a possible suspect material. This may be done automatically by comparing the detected radiation or contrast with a threshold, for example. Images may be generated and visually examined, as well.

A radiation beam path intercepting an HANM will typically intercept "background" material, such as agricultural materials or manufactured goods in front of and/or behind the HANM. The sensitivity and specificity of the scanning system 100 may be improved by normalizing for the background of the suspected HANM by separately calculating the TR of each pixel of a suspected HANM embedded within the background material, based on the transmitted radiation of the background material and the transmitted radiation for a combined suspected HANM and background material occupying the same beam path. Based on image processing techniques known in the art, such as segmentation, the boundaries of dense regions indicative of a possible HANM may be identified with respect to the background. Such dense regions may be identified in a prescan of the object being examined, at one of the energy endpoints, as discussed above. Then the transmitted radiation for each pixel through a dense region may be calculated by dividing the transmitted radiation of a pixel through the dense region by the transmitted radiation through the background, at each energy endpoint. The TR for each pixel in the dense region may then be calculated by dividing the adjusted transmitted radiations at each energy endpoint, as discussed above.

In order to have comparable statistical accuracy in the TR values for the dense region and the back ground, the size of the background is preferably selected such that the area of the background is about equal to or is the same order of magnitude as the area of the dense region. In one example, a predetermined area, such as the surrounding 1 to 5 centimeters of the contents in each direction outside the boundaries of the dense region, may be considered background material. The TR of the background material may be an average or other mathematical function of the TRs of the pixels forming the background. The median may also be used, for example. Two annular rings may be defined around the pixels of the dense region, for example. The annular ring closest to the dense region may be separated from the boundary of the dense region by 2 to 3 pixels in each direction, for example, to account for the imprecision of determining the exact boundary of the dense region. The next ring, which may encompass the same area as the suspect HANM, may be considered to encompass background material.

Figure 6B:
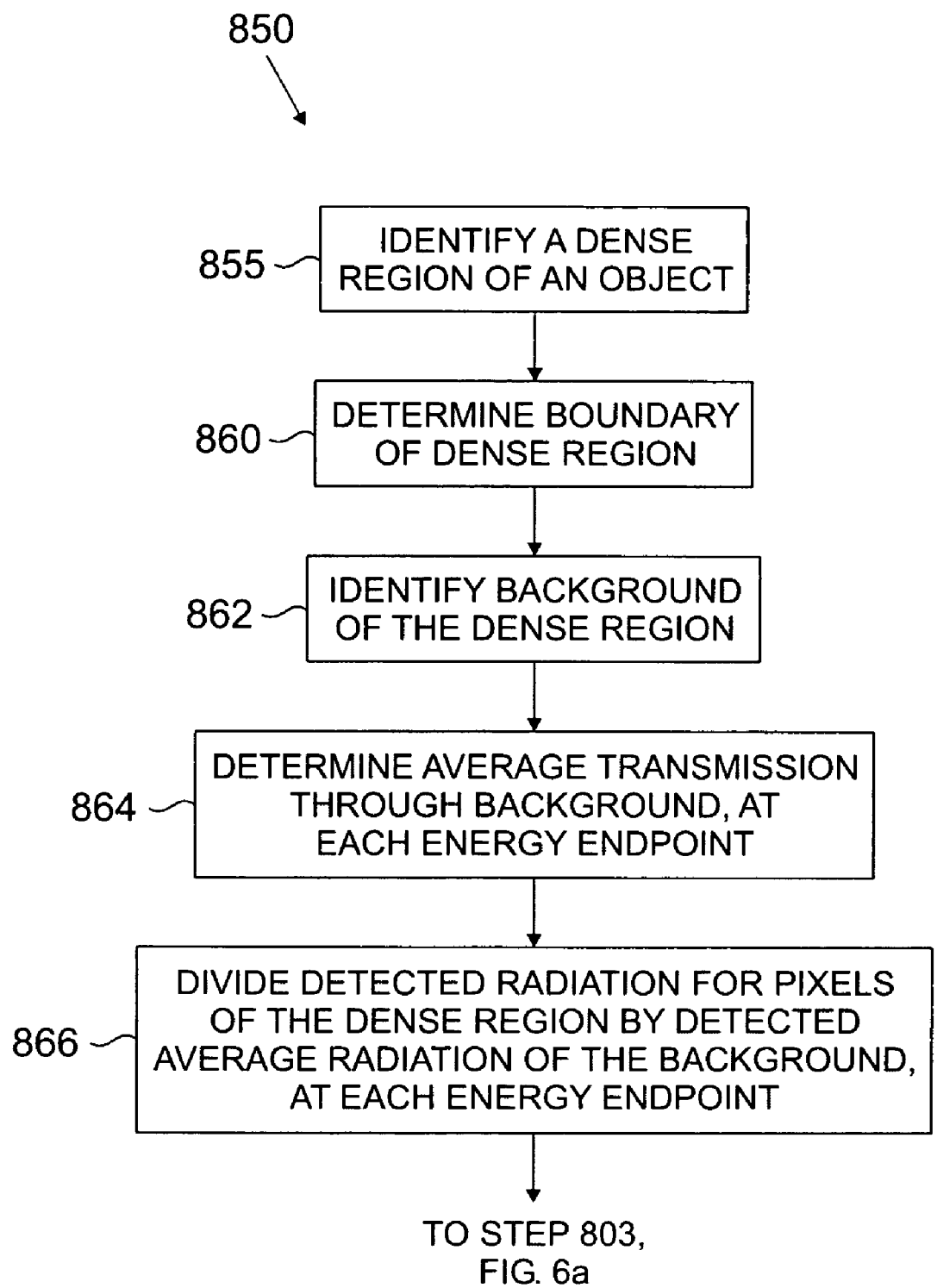
FIG. 6b is a flow chart of another example of a method to adjust detected radiation through a dense region of an image by background.

FIG. 6b is an example of a method 850 that may be executed by a processor, such as a computer, to adjust detected radiation through suspect dense regions of an object by the background of the dense regions. A dense region of an object is identified, in Step 855. The dense region may be identified in a prescan of the object at one of the energy endpoints, for example. The boundaries of the dense region are determined, in Step 860. Image processing techniques, such as segmentation, which are well known in the art, may be used, for example.

The background of the dense region is identified, in Step 862, and the average transmission through the background at each energy endpoint is determined, in Step 864, as discussed above. The detected radiation for each pixel of the dense region, which includes background along the beam path, is divided by the average detected radiation transmitted through the background, at each energy endpoint, in Step 866. The result is the transmitted radiation of the dense region at each energy endpoint, without the effect of the background along the beam path. The method may then proceed to Step 803 of FIG. 6a to calculate TRs for resultant pixels of the dense region based on the calculated transmissions for corresponding pixels, and to compare the TRs to thresholds.

The sensitivity and specificity of the determination that a low TR pixel is at least potentially indicative of an HANM based on the comparison of individual TRs to thresholds may not be sufficient for particular applications. Embodiments of the invention seek to further improve the specificity and sensitivity of this determination by increasing the number of pixels analyzed. A processor, such as a computer, of the scanning system may further analyze the resultant data in accordance with the embodiments of the invention, described below.

The Examination Window Test

In one embodiment of the invention, the number of pixels having TRs below the threshold ("low TR pixels") contained in a grouping of pixels having a predetermined area, referred to as an examination window, is examined. The examination window may be a 3 pixel×3 pixel or 9 pixel×9 pixel matrix of pixels, for example. A 9×9 pixel examination window W is shown in FIG. 2. If the number of the low TR pixels in the examination window exceeds a predetermined number, then HANM is considered to be present. The threshold value (average TR of a test piece minus/plus a value of standard deviations), the window size, and the minimum number of low TR pixels to be considered a threat may be chosen such that the probability that a non-HANM would meet the threat criterion, times the number of independent examination windows in an object (independent windows do not share common pixels) having at least one pixel below the threshold, is less than a desired sensitivity and specificity. Selection of the size of the examination window and the number of the standard deviations to be subtracted from the average TR of the test material to calculate the threshold is based on the following statistical analysis. This test is referred to as "the examination window test."

The size of the examination window may correspond to the cross-sectional area of the smallest HANM of concern that the scanning system can detect. HANM is typically smuggled in the shape of a sphere. The examination window may be the largest square fitting within a cross section of that sphere. Once the window size has been chosen, one chooses a threshold value and a minimum number of pixels below the threshold that if found will be considered a threat. Preferably, the smallest standard deviation is chosen because as the number of standard deviations increases, the probability of a response from a true HANM decreases. The threshold and minimum number are chosen such that the probability that a non-HANM will meet the detection criterion times the number of independent examination windows analyzed is less than a desired false alarm rate. An example of an acceptable false alarm rate is less than 1 in 100. Less than 1 in 1,000 is preferred. Less than 1 in 10,000 is more preferred.

In one example, a test piece of iron is scanned at the same two energy endpoints that will be used to scan cargo conveyances by that same scanning system. The TR measured at each pixel is considered to be an independent measurement of the TR for iron. For each value (integer or non-integer number) of standard deviations below the average TR of the test object, there will be a probability per pixel "p" that a single measurement will be less than the average TR minus that given value of standard deviations due to statistical fluctuations and not due to the presence of HANM. After "N" pixels are examined, there is a probability "P" that exactly "n" of these pixels will be below the threshold, also due to statistical fluctuations. This probability is given by the binomial distribution:

$$P(n \mid N) = \frac{N!}{n!(N-n)!} p^n (1-p)^{N-n}.$$

The probability of every expected outcome can therefore be calculated. Those low TR pixels that have some very small probability of occurring statistically, and therefore have a high probability of being a true HANM, may be identified. A false alarm rate, "$P_{fa}$" for a given situation is set and the probability of all the low TR pixels that would seem not to indicate the presence of a high atomic number material is evaluated. These probabilities are added until the difference between the sum and unity is less than $P_{fa}$. This sum of probabilities corresponds to the number of low TR pixels that will be false positives. Any number of low TR pixels above that corresponding number indicates the presence of a true HANM.

For example, assume a 9×9 pixel window and a threshold equal to the average TR for iron minus two standard deviations. Then the probability per pixel that a pixel is below the threshold due to statistical fluctuations is p=0.02275. The probability P(n/N) of seeing n pixels below the threshold in the 9×9 window due to statistical fluctuations is:

| n | P(n|81) | Sum of Probabilities |
|---|---------|----------------------|
| 0 | 0.1550 | 0.1550 |
| 1 | 0.2923 | 0.4474 |
| 2 | 0.2722 | 0.7197 |
| 3 | 0.1669 | 0.8865 |
| 4 | 0.0757 | 0.9623 |
| 5 | 0.0272 | 0.9894 |
| 6 | 0.0080 | 0.9974 |
| 7 | 0.0020 | 0.9994 |
| 8 | 0.0004 | 0.9999 |

The probability P(n/81) that eight (8) pixels will be found below the threshold due to a statistical fluctuation is 0.0004. The sum of probabilities that eight (8) pixels will be found below the threshold due to statistical fluctuation is 0.9999. Therefore, there is a 1 in 10,000 chance that if eight (8) or more pixels are found below the threshold, it is due to a statistical fluctuation and not to the presence of HANM. This is the false negative or false alarm rate $P_{fa}$, per examination window, based on eight (8) or more pixels. The probability that nine (9) or more low TR pixels are the result of a statistical fluctuation is less than the false alarm rate $P_{fa}$ of 1 in 10,000, in this example. Therefore, to achieve a false alarm rate $P_{fa}$ of less than 1 in 10,000, per window, then 9 or more pixels with a low TR need to be found in an examination window.

Figure 7:
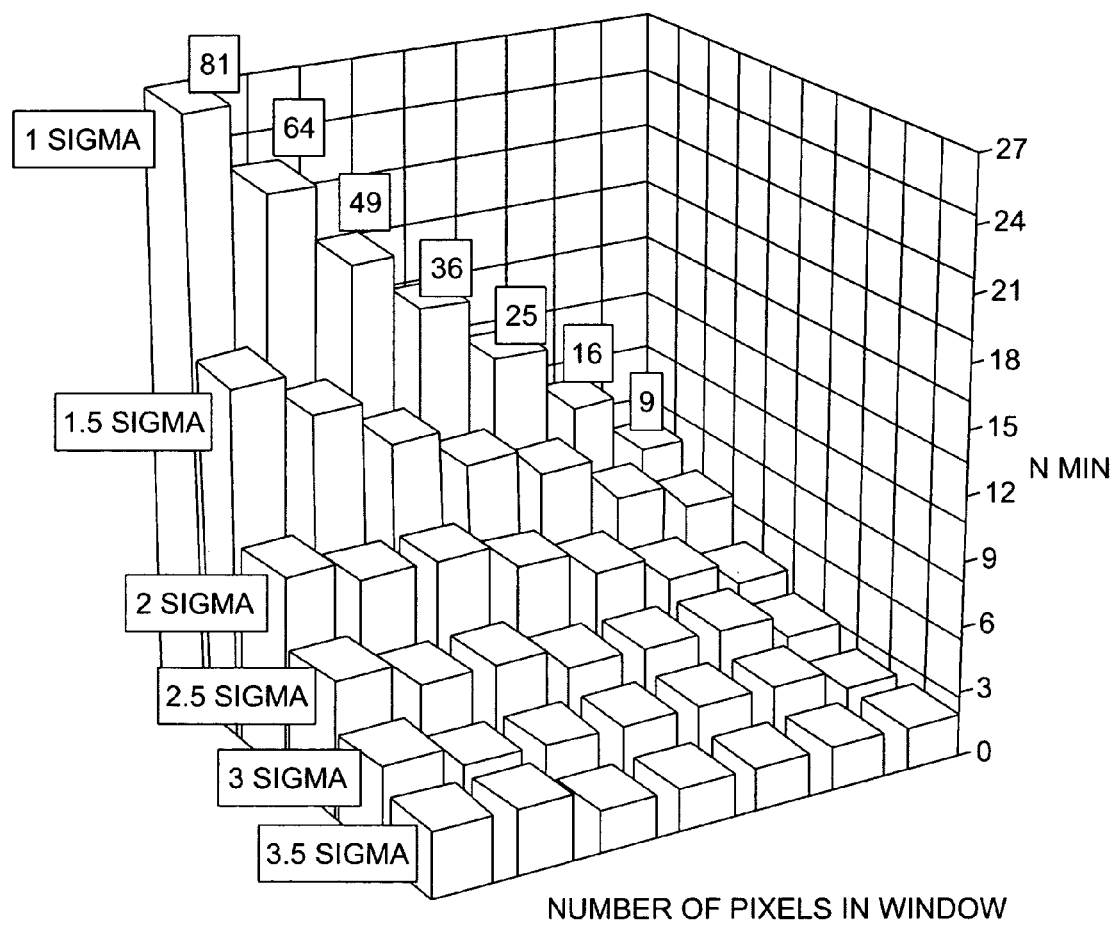
FIG. 7 is a bar chart of the minimum number of low TR pixels required to achieve a 1 in 10,000 false alarm rate for various sizes of examination windows and various standard deviations, in an embodiment of the invention.

FIG. 7 is a bar chart of the minimum number of low TR pixels required to achieve a 1 in 10,000 false alarm rate $P_{fa}$ for various sizes of examination windows and standard deviations. If one chooses a relatively large number of standard deviations (3 or more), for example, the examination window size may be relatively unimportant because the minimum number of pixels required to indicate HANM at that false alarm rate $P_{fa}$ changes by only a small amount (a fraction of a pixel). If one uses a fairly small number of standard deviations, such as 1, then the minimum number required to indicate the presence of HANM at a particular false alarm rate $P_{fa}$ is a fairly strong function of the examination window size. For example, with a 9×9 matrix window size and 1 standard deviation, 27 pixels are required to indicate HANM with the false alarm rate $P_{fa}$ of 1 in 10,000. With an 8×8 matrix window size, 24 pixels are required.

Two examinations may be conducted, one with a larger examination window, to detect larger masses of HANM, and another with a smaller window, to detect smaller masses. As discussed above, in this system, a 9×9 matrix may be used to detect larger masses. The smaller window may be a 3×3 matrix, for example. With a 3×3 matrix, the number of standard deviations subtracted from the average TR of the test object may be 2 or 2.5, for example. At 2.5 standard deviations and a 3×3 matrix, the presence of 3 pixels below the threshold would indicate HANM with a false positive rate of 1 in 10,000, as shown in FIG. 7. The examination window test may be the sole test for determining whether an HANM is present, or it may be used in conjunction with other examination techniques, including the other embodiments of the invention discussed below.

The entire object may be examined by analyzing an examination window moved across the TRs of the object. For example, the window may be positioned starting in one location, such as in a corner of the object, and then moved to the opposite corner, one column of pixels at a time. Subsequently, the examination window may be moved down by one row of pixels and then across the TRs, one column of pixels at a time. The pixels in each window are analyzed and the analysis ends when all the possible examination windows of the object have been analyzed.

In an example of an implementation of the examination window test, during operation of the cargo scanning system, the cargo conveyance is subjected to two X-ray radiation beams, each with a different energy endpoint, such as at 9 MeV and 5 MeV. The radiation at each radiation endpoint is detected by a detector after interaction with the cargo conveyance. An example of a cargo scanning system that may be programmed to implement this and other embodiments of the invention is discussed below.

Figure 8:
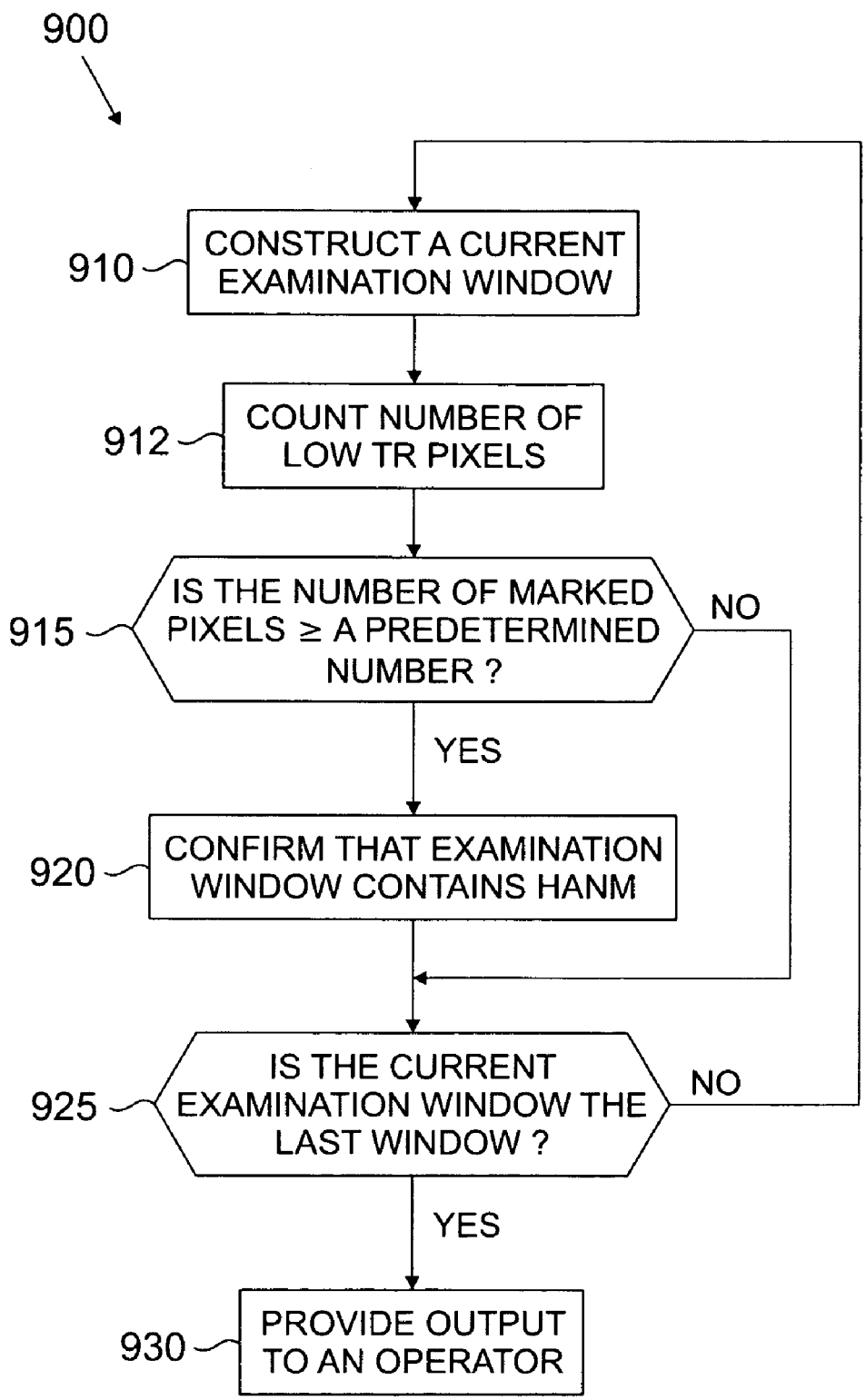
FIG. 8 is a flow chart of an example of an "examination window test," in accordance with the embodiment of FIG. 7.

FIG. 8 is an example of a method 900 that may be executed by a processor, such as a computer, for example, to implement the examination window test. After calculation of the TRs of the resultant pixels, in the method 800 of FIG. 6a (and optionally in conjunction with the method 850 of FIG. 6b), for example, the computer selects a pixel and constructs an examination window, such as a 9×9 matrix, centered about the selected pixel, in Step 910. The computer identifies a number of the low TR (marked) pixels in the examination window, in Step 912, and compares it with a predetermined number, in Step 915. The predetermined number is the highest statistically determined number of low TR pixels that can be false positives (a pixel having a low TR even though the pixel is not an HANM), under the selected conditions, as discussed above. Computation of the threshold is described further below, with respect to FIG. 13, for example.

If the number of low TR pixels is greater than or equal to the predetermined number, an area of the cargo conveyance corresponding to the low TR pixels is classified as an HANM, in Step 920. If the number of the low TR pixels in the examination window is less than the predetermined number, it is determined whether the current examination window is the last examination window to be analyzed, in Step 925.

If not, the examination window is shifted one column of pixels to the left one row of pixels down, as appropriate, to construct a new current examination window, in Step 910. Then the computer repeats all the steps of the method 900, as described above. The method 900 may be repeated with a smaller examination window, different number of standard deviations and different predetermined number. If the current examination window is the last window to be analyzed, an output is provided to an operator, in Step 930.

Figure 9:
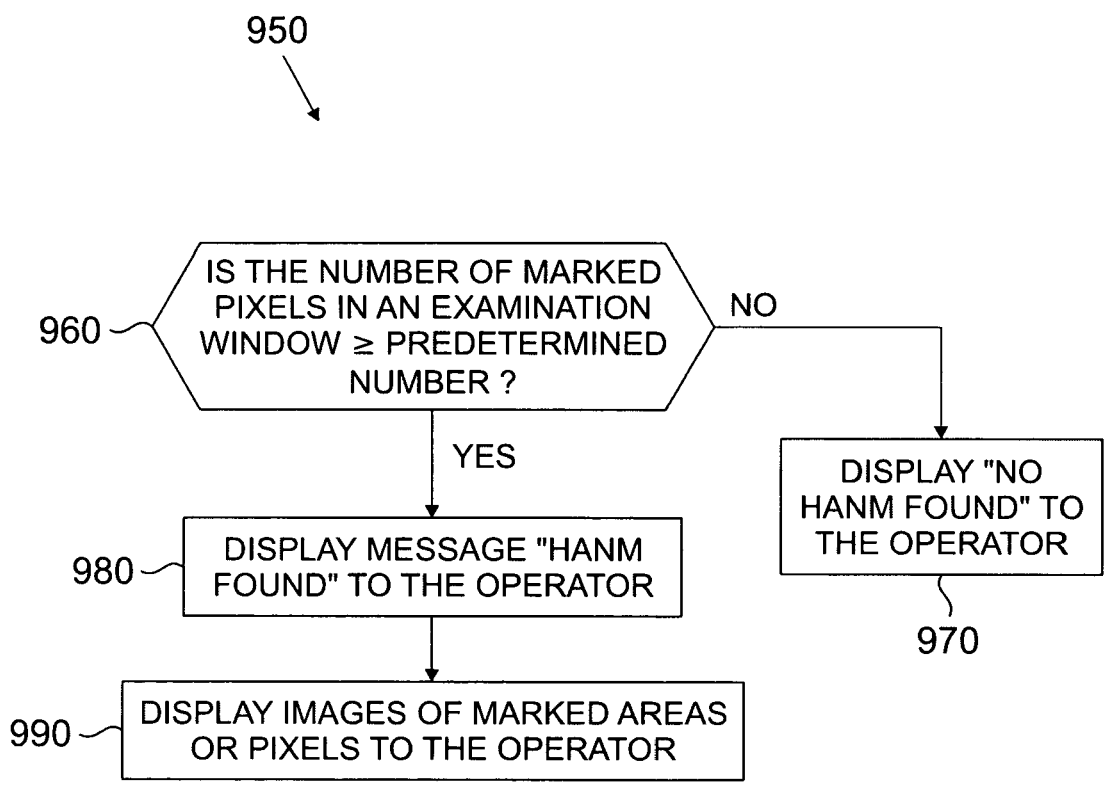
FIG. 9 is a flow chart of an example of a method for providing an output of an examination to an operator, in accordance with embodiments of the invention.

FIG. 9 is an example of a method 950 that may be executed by the processor, such as a computer, to display the results of the analysis to the operator of the cargo scanning system 100. In Step 960, the processor checks whether there are any examination windows with a number of marked pixels greater than or equal to the predetermined number, as determined in Step 915 of the method 900, for example. If the number of marked pixels, if any, is not greater than or equal to the predetermined number in any examination window, the processor proceeds to Step 970 and displays a message "No HANM." If the number of marked pixels in any examination window is greater than the predetermined number, the processor proceeds to Step 980 to display a message "HANM Found," for example, thus alerting the operator to the presence of a high atomic number material in the cargo conveyance. The processor may also display the images of the examination window or windows showing the presence of an HANM, in Step 990. An entire image including the windows may be displayed instead of or along with the images of the windows, as well.

If the output indicates that HANM is present, the operator may then have several options. For example, a manifest for the cargo conveyance may be checked to determine whether HANM has been properly declared and is not a threat. The HANM may be an HANM but not a radioactive material, for example, such as silver for industrial or medical use, which should be identified on the manifest. The HANM may also be a radioactive material for medical use, which should be declared on the manifest. The operator may also cause the scanning unit and the processor to perform additional scanning of the cargo conveyance and/or mathematical analysis of measurements, including other tests discussed herein, and/or the operator may conduct a manual inspection of the cargo conveyance. A cargo conveyance failing inspection due to the suspected presence of HANM may be removed from the area and dealt with in accordance with known procedures.

If the output is not indicative of the presence of HANM, the cargo conveyance may be considered to "pass" the inspection. However, if the operator still suspects HANM are present (based on the prescan, for example), the operator may still conduct a manual inspection. Also, if the method 850 of FIG. 6b was not used in conjunction with the calculation of TRs in the method 800 of FIG. 6a, the method 850 may be conducted, the TRs recalculated, and then analyzed as described above. If HANM is still not shown, any or all of the the other tests described herein, or other tests known in the art, may be conducted. Once the operator is satisfied, the cargo conveyance may be "passed."

The Contiguity Test

Once a first resultant pixel meeting the test criterion is found (as described with respect to FIG. 6a, for example), another way to increase the number of resultant pixels analyzed is to analyze the pixel's environment to identify pixels contiguous to that pixel that also meet the test criterion. Analyzing the environment of that first resultant pixel increases the statistical accuracy (decreases the standard deviation) of the measurements because it is more likely that the first pixel is part of an HANM if contiguous pixels are also part of an HANM. Analyzing pixels surrounding the first pixel also effectively increases the number of photons contributing to a determination. If the area of the contiguous pixels is greater than or equal to a predetermined area, the identification of HANM has greater sensitivity and specificity than a determination based on a single pixel or a grouping having an area less than the predetermined area.

The predetermined area may be a cross-sectional area of the smallest HANM capable of producing a self-sustaining nuclear reaction. For example, the area may be 20.25 $cm^2$, which is the area of a 4.5 cm×4.5 cm square. A square of this size is representative of a cross-sectional area of the smallest sphere encompassing a square of these dimensions. The size of the area may be determined by counting marked pixels. (See Step 815, FIG. 6a, discussed above, where low TR pixels are marked.) Other smaller or larger areas may be used as well. The area of the contiguous pixels need not be in the shape of a square.

If contiguous pixels covering an area greater than or equal to the predetermined area are found, then an HANM is considered to be at least potentially present. In one example, pixels sharing an edge, such as a pixel G and a pixel H in FIG. 2, are considered to be contiguous, while pixels sharing only a vertex, such as pixels F and G, are not. A different definition of "contiguous" may be used, which may include pixels sharing a vertex, for example. This embodiment of the invention is referred to as the "contiguity test." Comparison based on the area, rather than shape, is believed to be more reliable, but shape may be considered as well.

Figure 10:
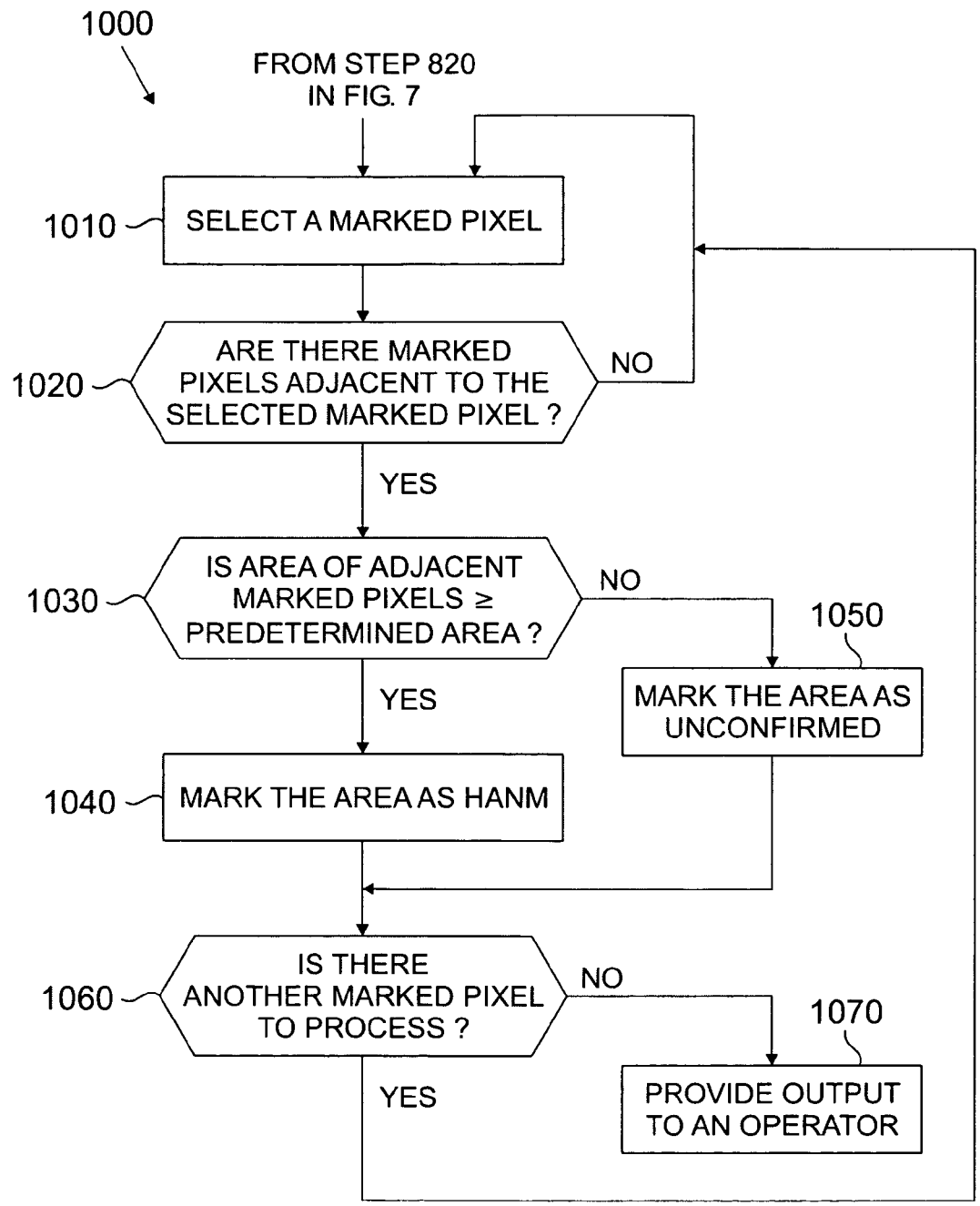
FIG. 10 is a flow chart of an example of a "contiguity test," in accordance with another embodiment of the invention.

FIG. 10 is an example of a method 1000 that may be executed by a processor, such as a computer, to implement the contiguity test. A marked pixel is selected, in Step 1010. It is determined whether there are additional marked pixels contiguous to the selected pixel, in Step 1020. Pixels in the array are checked and accumulated in all directions from the selected marked pixel until a first "unmarked" pixel (whose TR is above threshold) is reached in every direction. Algorithms for such analysis are well known in the art.

If there are marked pixels contiguous to the selected marked pixel, the size of the area of the contiguous marked pixels is compared to a predetermined area, such as the area of the smallest HANM the system 100 is designed to detect, in this example a 20.25 $cm^2$, in Step 1030. The area covered by the marked pixels "accumulated" in Step 1030, is preferably determined by counting marked pixels, for example. If each pixel is 0.5 cm×0.5 cm, the area covered by 81 contiguous marked pixels centered around the pixel A shown in FIG. 5, for example, is equal to 20.25 $cm^2$ (4.5 cm×4.5 cm). While in the example the area is a square, that is not required. If the condition in Step 1030 is satisfied, the area of the contiguous marked pixels is marked as an HANM, in Step 1040. Optionally, an image of this area may be generated for display to an operator.

If the area covered by the marked pixels is less than the predetermined area, the area of adjacent marked pixels is marked as unconfirmed HANM, in Step 1050. After either Steps 1040 or 1050, it is determined whether there is another marked pixel to process, in Step 1060. If so, a new marked pixel is selected, in Step 1010, and the method 1000 is repeated. If there are no other pixels to process, then the condition in Step 1060 would not be satisfied and the computer provides an output to the operator, in Step 1070. It is noted that once an individual pixel is part of a previously marked area, it need not be further analyzed by this process (although it may be). Therefore, Step 1010 may be limited to selecting a marked pixel that is not part of a previously marked area. Step 1060 may be similarly limited to determining whether there is another marked pixel not part of a previously marked area.

The contiguity test may be used alone or in conjunction with other examination techniques, including the other embodiments tests described herein. The operator may respond to the output provided, as described above with respect to the examination window test.

Analyzing the environment of a suspect resultant pixel is also useful where only a limited number of photons may be detected at each resultant pixel. For example, certain non-threatening materials (non-HANMs), such as agricultural goods, may be very dense. Low TR pixels may be found even though the material is not an HANM, because of the low transmission through the dense material causes a high statistical inaccuracy. The contiguity test may improve the statistical accuracy of the determination based on measured radiation at a pixel by considering the radiation detected in the environment of the pixel, as well.

The Matrix Test

In another embodiment, resultant pixels are grouped and a function of the TRs in the group is analyzed. The function may be an average or median of the TRs in the group, for example. The group may be formed about a suspect pixel or a plurality of groupings may be provided to encompass all the pixels. The grouping may be a matrix, for example. This test is therefore referred to as the "matrix test."

Figure 11:
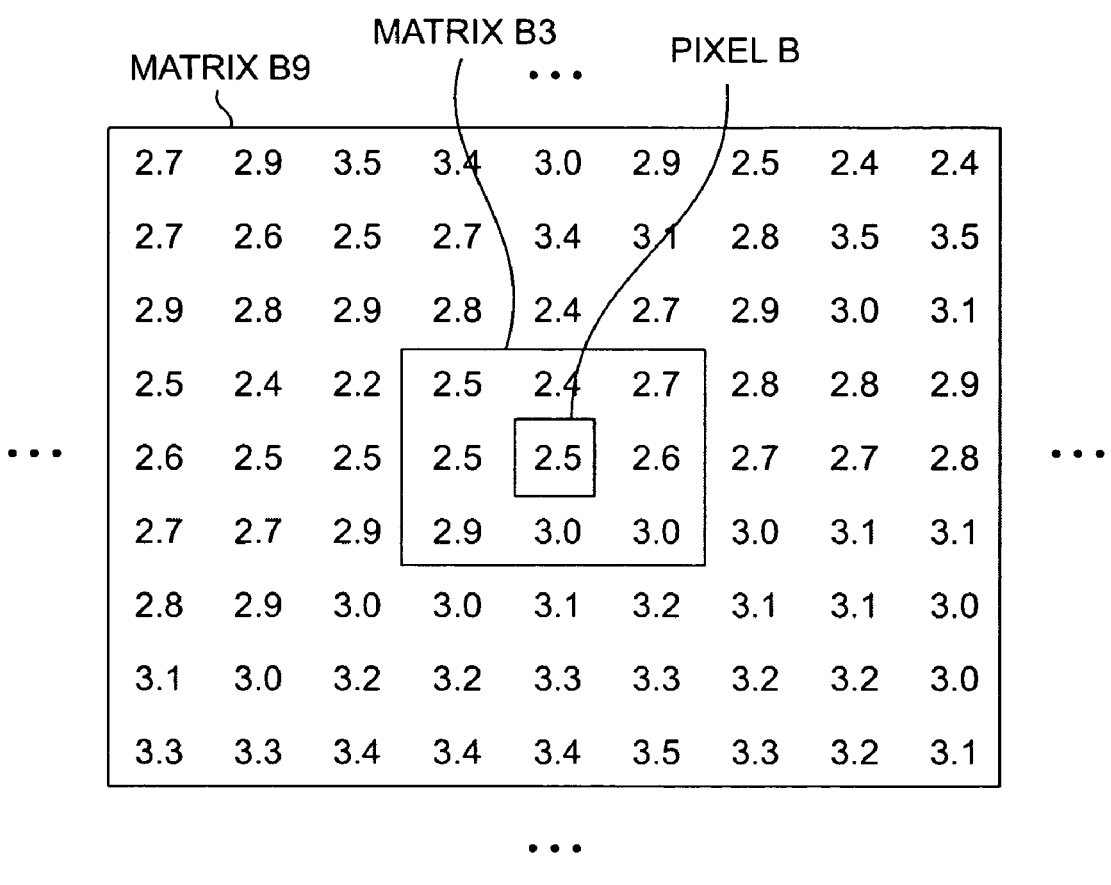
FIG. 11 is an example of an array of TRs for a group of pixels representing a portion of a cargo container, for use in embodiments of the invention.

The item 410 in FIG. 2 is an example of another item within the cargo conveyance 10. The pixel B is a low TR, and therefore suspect pixel, within the item 410. The 3×3 pixel matrix B3 in FIG. 2 is an example of a grouping, "constructed" around the pixel B. FIG. 11 is an example of an array of the TRs for a portion of the cargo conveyance 10, showing the low TR pixel B and the matrix B3. The average TR, for example, of the matrix B3 is calculated by averaging the TRs of each pixel in the matrix. The average TR is then compared to the threshold. If the average is below the threshold, HANM may be considered to have been found. In one example, where the pixel size is 0.5 cm, the 3×3 pixel matrix B3 may be used to identify a potential HANM having a cross-sectional area of at least about 1.5 cm×1.5 cm. The threshold used in the comparison may be selected based on the average or other such function of the transmissions of the pixels in the matrix.

The statistical accuracy of the TR for the 3×3 matrix is three times greater than the statistical accuracy of the TR for the individual low TR pixel. Since false positives may cause unnecessary, costly, time consuming, and disruptive inspection of the cargo conveyance, additional confirmation, with even greater accuracy, is preferably obtained before a definitive finding is made that the pixel B belongs to an HANM.

To further improve the accuracy of the determination (to decrease the standard deviation) for larger objects, after the 3×3 matrix is examined, an even larger matrix, such as a 9×9 pixel matrix B9, which is also shown in FIG. 2 and FIG. 11, is preferably created, centered around the same selected low TR pixel B. Other size matrices, such as 5×5 and 7×7 pixel matrices, may be constructed, instead or as well. The size of the larger matrix may depend on the size of the items to be identified and the size of the pixels. The 9×9 pixel matrix B9 contains eighty-one additional adjacent pixels with data contributing to the determination of whether HANM is present. An average of the TRs of the pixels of the larger matrix is generated and is similarly compared to the threshold. If both the average TRs of the first and second matrices are below the threshold, the current low TR pixel is determined with even more confidence to represent an HANM. In this example, the 3×3 pixel matrix B3 provides a first identification of a potential HANM, whose presence is verified with greater confidence by the 9×9 pixel matrix B9.

The analysis continues until all the low TR pixels have been processed. Multiple overlapping 3×3 matrices, as well as overlapping 9×9 matrices, may be constructed across an array. FIG. 2 shows an additional 3×3 matrix B4, for example, which overlaps the matrix B3.

In another example, if the detector elements are 1.5 cm×1.5 cm and a pixel size is 1.5 cm, a 3×3 pixel matrix would encompass a 4.5 cm cube of HANM. If the detector element is 0.1 cm and the pixel size is 0.1 cm, a 45 pixel×45 pixel matrix would be required to encompass a 4.5 cm cube of HANM, or HANM covering an area of 20.25 cm.

Figure 12:
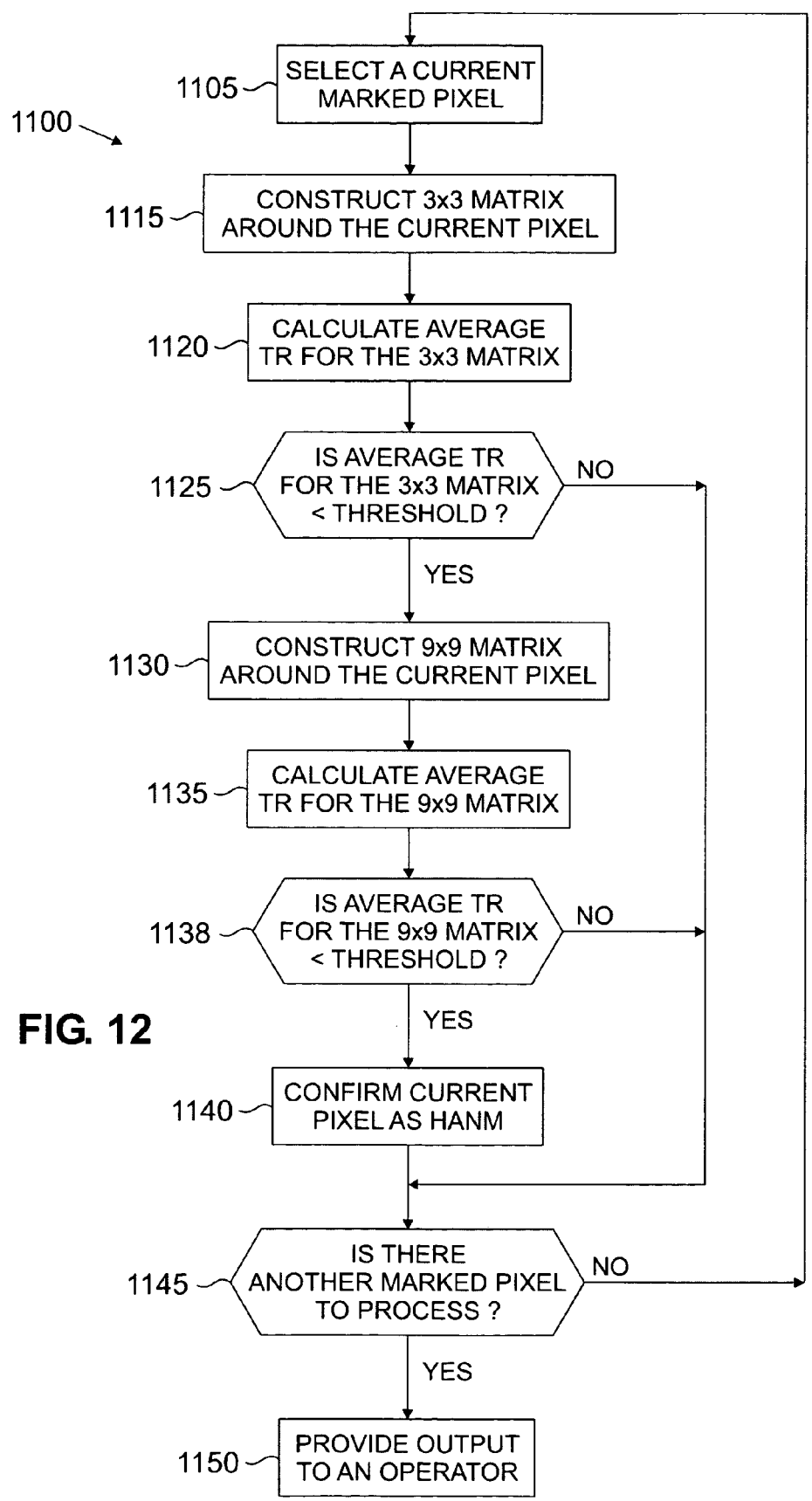
FIG. 12 is a flow chart of an example of a "matrix test," in accordance with the embodiment of FIG. 11.

FIG. 12 is an example of a method 100 that may be executed by a processor, such as a computer, to implement the matrix test. In this example, the pixel size is 0.5 cm×0.5 cm. After executing the method 800 in FIG. 6a to identify and mark low HANM pixels, and optionally after implementing the contiguity test, an example of which is shown in the method 1000 of FIG. 10, a current marked pixel is selected, in Step 1105. The low TR pixel B within the object 410 in FIG. 2, is selected, for example. A 3×3 matrix B3 centered around the pixel B is "constructed" (see FIG. 11), in Step 1115, to identify HANM encompassing an area of 0.5 cm×0.5 cm, and larger.

The average TR for the matrix B3 is then calculated by summing the nine TRs in the matrix B3 and dividing that sum by the number of individual pixels, in Step 1120. In this example, the average TR for the matrix B3 is 2.7. It is then determined whether the average TR of the matrix B3 is below the threshold, in Step 1125. The threshold in this example is 3.9. Since 2.7 is less than 3.9, the condition is satisfied. This means that the matrix B3 represents an HANM with an accuracy of three times that of the accuracy of the initial suspicion that pixel B may be an HANM based solely on the fact that pixel B had a low TR.

In this example, for an HANM encompassing a cross-sectional area of 4.5 cm×4.5 cm and larger, a 9×9 matrix B9 is also preferably constructed centered around the pixel B in Step 1130, to provide greater sensitivity and specificity to a finding of HANM by the 3×3 pixel matrix. An example of a 9×9 matrix B9 is shown in FIG. 12. The average TR for the matrix B9 is calculated in Step 1135. The TRs in the matrix B9 are summed and the sum is divided by 81 (the number of individual pixels). In this example, the TR for the matrix B9 of FIG. 11 is 2.9. Since nine (9) times as many pixels are considered, the statistical probability of the accuracy of the TR for the matrix B9 is three times greater than the statistical probability of the accuracy of TR of the matrix B3. The TR of the matrix B9 is compared to the threshold, in Step 1138. It is then determined whether the average TR is less than the threshold, in Step 1138. If so, then it is confirmed that the current marked pixel corresponds to an HANM, in Step 1140, with a higher degree of sensitivity and specificity. Since 2.9 is less than 3.9, the condition is met. It is then determined whether the pixel B is the last marked pixel to analyze, in Step 1145. Since there are other marked pixels to be analyzed, the condition is not satisfied, the method returns to Step 1105, and the method 1100 is repeated for the next marked pixel.

If the TR of the matrix B9 is not less than the threshold, then the pixel B is not confirmed as an HANM in Step 1140 and the method proceeds to Step 1145, as discussed above. After all the TRs of all the marked pixels are analyzed, the condition in Step 1145 becomes true and an output is provided to the operator: The operator may respond to the output as described above with respect to the examination window test.

It is believed that the matrix test may identify a cube of HANM with sides of 4.5 cm, such as an uranium cube, behind a 20 cm thick shield of iron, for example. The matrix test may be performed alone or in conjunction with any or all of the other tests described herein, or other tests known in the art. For example, if the area of the item 410 is less than the predetermined size of the contiguity test, discussed above, it would not be identified as an HANM by that test. It could still be a dangerous HANM, however, as several objects of an SNM may be smuggled in one or more cargo conveyances and combined into a single object large enough to sustain a nuclear reaction. An HANM smaller than the predetermined size could also be used in a "dirty" bomb. Items smaller than the predetermined area of the contiguity test may be identified by the matrix test using a matrix smaller than the predetermined area of the contiguity test. When the matrix test is being used to examine low TR pixels in areas less that the predetermined size of the contiguity test, only low TR pixels not part of an object greater than the predetermined size need to be selected for analysis by the matrix test, but that is not required.

It is noted that for smaller items, where only a small matrix (such as the 3×3 pixel matrix B3) encompasses enough of an item to at least potentially identify the item as an HANM, the identification of HANM may not be as reliable as if larger matrices are also used. Such potential identification may, however, justify further examination, such as conducting the other tests described herein or known in the art, checking the manifest, and/or conducting a manual examination. It is also noted that an average or other such function of TRs of groupings other than a matrix may be compared to a threshold to determine whether the grouping is at least potentially HANM. For example, the grouping may be the dense regions identified in a prescan, as discussed above. The boundaries of the dense region may be defined as discussed above, the TRs of the pixels of the dense region may be averaged, and the average compared to the threshold.

Threshold Calculation

As discussed above, the threshold for separating an HANM from a non-HANM is preferably calculated for each scanning system. Threshold calculation may take place when a cargo scanning system is periodically calibrated. The calculation depends, in part, on the desired degree of sensitivity and specificity for the system. As discussed above, the threshold may be determined by scanning a test material having an atomic number less than the lowest atomic number of a material of concern (such as uranium) at the same two energies as will be used to scan cargo conveyances. Preferably, the test piece also has an atomic number greater than or equal to that of common allowable materials, to avoid false positives. Iron, nickel, and copper are examples of preferred test materials.

The test piece preferably has a varying thickness, so that thresholds may be calculated at different transmission through the test piece. The test piece may be wedge shaped or step shaped, for example. The thicknesses may correspond to the expected range of transmissions of acceptable materials and HANMs. Thresholds calculated at the different thicknesses may be used with the test criteria applied to resultant pixels having corresponding transmissions. The test piece may have a thickness of from about 1 mm to about 400 mm, for example. The transmission at either energy endpoint may be used. If the test piece is step shaped, the standard deviation is calculated for the TRs across each step. If the test piece is wedge shaped, the standard deviation is calculated for TRs through a particular thickness of a portion of the wedge. One or a few columns of data may be used for each thickness. This standard deviation is used during examination of an object to interpolate between measured transmissions, to calculate a threshold between calculated thresholds based on the test piece. Alternatively, the calculated threshold closest to the measured transmission may be used, but that may not be as precise.

The TRs are calculated, summed, and averaged, at each thickness. As is known in the art, the probability that a measurement is a statistical variation of a measured quantity, such as TR, is a function of the distance between the arithmetic mean of the distribution of the measurements and the measurement in question. This distance is measured in standard deviations. Such probabilities are expressed in tables and are well known in the art. For example, a measurement that is three standard deviations from the arithmetic mean of a plurality of measurements has about a 0.0013 probability of being a statistical variation. This probability is the false alarm rate, which in this example is 13 in 10,000. Therefore, to reduce the probability that the TR is a statistical variation of the actual TR with a 0.0013 probability of being incorrect, in this example three standard deviations are selected for the calculation of the threshold, at each thickness. The value of standard deviations used may be an integer, in this example, 3, or it may be a non-integer, such as 2.5, for example. The same standard deviation is preferably used at each thickness.

To achieve a different sensitivity and specificity, a different value of standard deviations may be subtracted from the average TR of the low atomic number material of the test piece, at each given that any given measurement of transmitted radiation may be from an HANM or a non-HANM, the number of standard deviations to be subtracted from the TR of a low atomic number material is selected to achieve a desired balance between an acceptable number of false positives and false negatives. For example, subtracting eight standard deviations from the TR of a low atomic number material would result in zero (0) false positives but possibly an unacceptable number of false negatives. As mentioned above, if a greater number of false positives may be tolerated, then it may not be necessary to take into consideration the standard deviation.

If the measurement at the higher energy endpoint is divided by the measurement at the lower energy endpoint, then the standard deviations are subtracted from the average TR of the test piece. If the measurement at the lower energy endpoint is divided by the measurement at the higher energy endpoint, the value of standard deviations is added to the average TR of the test piece. The specific number of standard deviations will determine the sensitivity and specificity of the systems.

Figure 13:
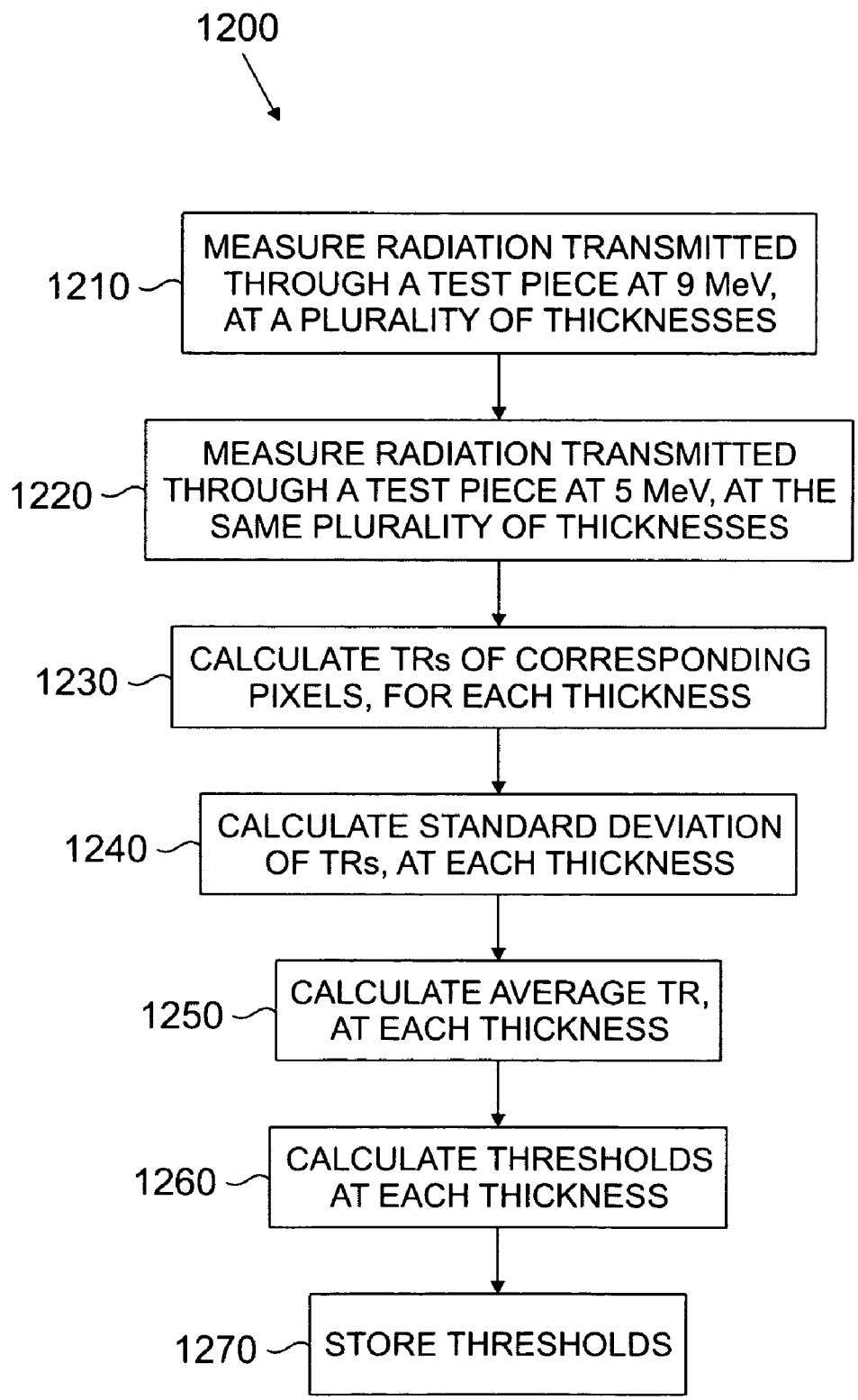
FIG. 13 is a flow chart of an example of a method for calculating thresholds, in accordance with an embodiment of the invention.

FIG. 13 depicts an example of a method 1200 that may be implemented by a processor, such as a computer, to calculate the thresholds. A test piece is scanned by the cargo scanning system with radiation having a first, high energy endpoint, such as 9 MeV, at a plurality of thicknesses, in Step 1210. The radiation transmitted through the test piece is detected for each pixel, also in Step 1210. Scanning may be conducted at 5 MeV first, instead.

The test piece is then scanned with a second radiation beam having a second energy endpoint less than the first energy endpoint, such as 5 MeV, and the radiation transmitted through the test piece at the plurality of thicknesses is detected for a plurality of pixels corresponding to the pixels of Step 1210, in Step 1220. The TRs for resultant pixels are calculated by dividing the transmitted radiation measured at 9 MeV by the transmitted radiation measured at 5 MeV (or vice versa) for the corresponding pixels, in Step 1230.

The standard deviation of the calculated TRs is determined, in Step 1240. Preferably, the standard deviation is calculated for the TRs at each thickness of the test piece for use in interpolating between calculated thresholds during actual measurements. Standard deviation may be calculated according to the following formula:

$$S = \sqrt{\frac{\sum_{i=1}^{N}(x_i - \bar{x})^2}{N-1}},$$

where $x_i$ is the measured attenuated radiation for a pixel i, $\bar{x}$ is the arithmetic mean (average) of the measured attenuated radiation for all the pixels, which is calculated according to the formula $$\bar{x} = \frac{\sum_{i=1}^{N} x_i}{N},$$

and N is the number of pixels. In this illustrative example, the standard deviation of the test measurements of transmitted radiation is calculated to be 0.2. Other statistical methods may be used with different distributions of the measured attenuated radiation.

The average TRs of the TRs at each thickness are calculated, in Step 1250. The threshold is calculated at each thickness in Step 1260. Preferably, the thresholds are calculated by adjusting the average TR at each thickness of the test piece by an integral or non-integral number of standard deviations, dependent upon the desired sensitivity and specificity, in Step 1250. The calculated thresholds are stored, in Step 1270. The thresholds may be stored in association with corresponding transmissions and standard deviations for each thickness of the test piece a database of thresholds, for example.

Using a threshold based on the average TR of iron, which may be about 4.5, to differentiate a 4.5 cm×4.5 cm HANM, which may have a TR of about 2.5, embedded within a 2 meter cube of agricultural goods, which may have a TR of about 7, may be difficult. Since an HANM typically has an atomic number that is further from the atomic number of typical agricultural goods than the atomic number of iron, it is easier to differentiate an HANM from agricultural goods than from iron with the required degree of statistical accuracy. To improve sensitivity and specificity of the identification of HANM, thresholds may be selected based on the contents of the cargo conveyance being examined. Therefore, if it is known that a cargo conveyance contains agricultural goods, the TR of agricultural goods, or a material representative of agricultural goods, such as a plastic or water, may be used in determining the threshold, instead of the TR of iron or other such materials. Lucite (R) or Delrin (R) may be used, for example. A test piece of varying thickness is preferably used, as discussed above. The calculated thresholds may also be stored in the database of thresholds for use in the examination techniques discussed above.

Sufficient information about the contents of the cargo conveyance may be available through the customs manifest, for example. A typical manifest filed by the shipper or owner of the cargo conveyance declares the type of goods that are supposed to be shipped in the cargo conveyance, such as agricultural goods, manufactured goods, etc.

Figure 14:
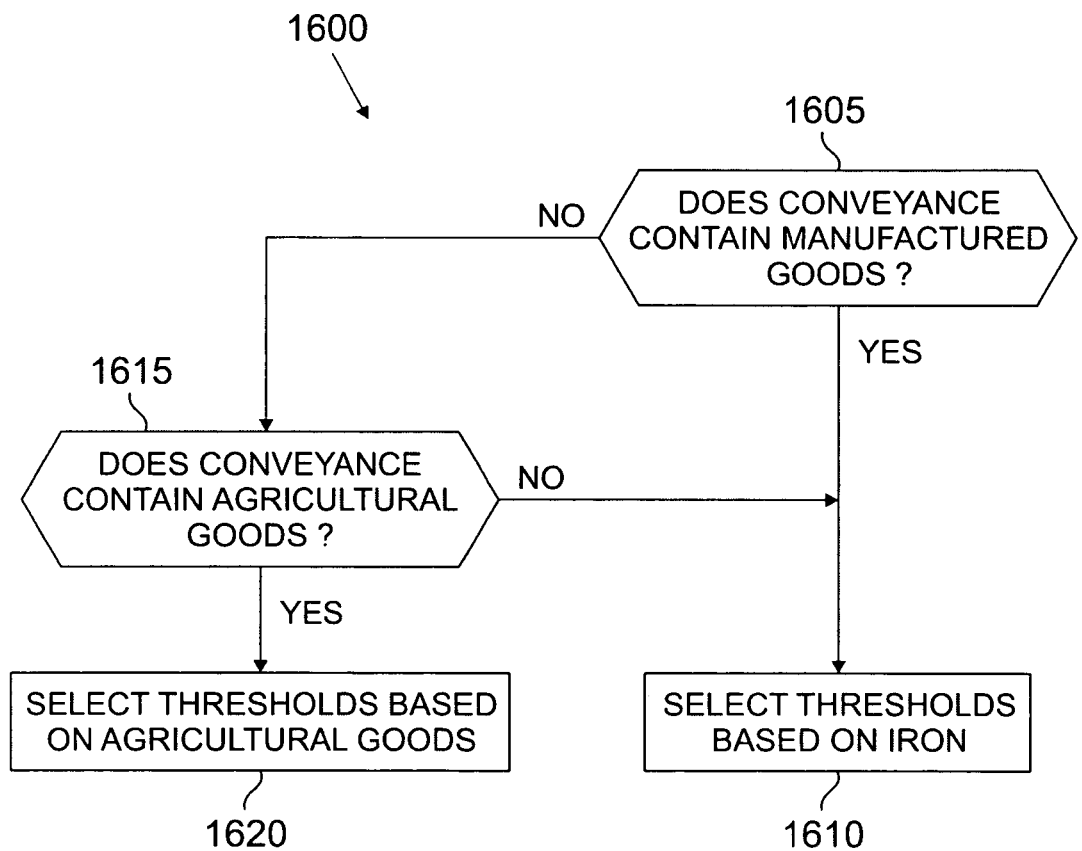
FIG. 14 is a flow chart of an example of a method for selecting a threshold based on the contents of a cargo conveyance, in accordance with another embodiment of the invention.

FIG. 14 is an example of a method. 1600 to select a threshold based on the type of contents declared in the manifest. The manifest is checked to determine if the cargo conveyance 104 contains manufactured goods, in Step 1605. If it does, then thresholds based on iron and the detected transmission, as discussed above, for example, are selected as the thresholds to be used in analyzing the contents of the cargo conveyance 104, in Step 1610. The thresholds may be based on copper or nickel, instead. If the manifest does not indicate that the cargo conveyance contains manufactured goods, it is determined whether the manifest indicates that the cargo conveyance contains agricultural goods, in Step 1615. If it does, then a threshold based on agricultural goods is selected for use in analyzing the contents of the cargo conveyance. If it does not, then a threshold for iron is selected, in Step 1610. The method 1600 may be implemented by an operator reviewing a manifest for the cargo conveyance being inspected. The operator may then input which threshold, or groups of thresholds, are to be used in the tests described above. A processor, such as a computer, may implement the method 1600, if the manifest has been electronically entered, for example.

Nuclear Test

Other X-ray scanning and/or analysis techniques may be used in conjunction with the grouping related techniques described above, to further increase the accuracy of the conclusion that the suspect pixel or pixels are HANM, and to reduce the false alarm rate. The tests above determine whether any material within a cargo conveyance is classifiable as HANM. An HANM may be a nuclear material (fissionable, fissile, or fertile material), the presence of which needs to be identified with a high degree of sensitivity and specificity. As discussed above, uranium-235, plutonium-239, and uranium-233 are examples of fissile materials. Fissionable materials include fissile materials and uranium-238. Fertile materials include uranium-238, which is convertible into plutonium-239, and thorium-232, which is convertible into uranium-233. Certain fissile materials that more readily undergo fission than others are referred to as Special Nuclear Materials ("SNMs"). SNMs are currently defined by the U.S. Nuclear Regulatory Commission to include plutonium, uranium-233, or uranium enriched in the isotopes uranium-233 or uranium-235. Nuclear materials emit delayed neutrons due to beta decay after fission of their nuclei caused by exposure to X-ray radiation of sufficient energy, 1–2 μs after exposure, as is known in the art. Since non-nuclear materials do not emit delayed neutrons, the presence of delayed neutrons may be used to identify the presence of nuclear materials. Delayed neutrons may be detected and counted by a neutron detector, for example. Neutron detectors are discussed further, below.

The minimum energy required to induce photofission in nuclear materials, referred to as the photofission or fission threshold, depends on the material. Table I identifies fission thresholds for selected elements, calculated based on mass excess values for the selected elements. The mass excess values were obtained from Nuclear Wallet Cards, available from NNDC Brookhaven Laboratory, January, 1985. A current edition of the Nuclear Wallet Cards is available at www.nndc.bnl.gov/wallet/wallet-2000.pdf. It is noted that both nuclear materials and non-nuclear materials may also produce photoneutrons within a very short period ($10^{-15}$ sec) of exposure to X-ray radiation. Photoneutrons are absorbed by the materials in the container and the components of the X-ray scanning system. Table I shows the thresholds for photoneutron emission for the selected nuclear materials, as well. The photoneutron data was obtained from T-2 Nuclear Information Service, Los Alamos, at http://+2.1an/gov/data/photonuclear.html. Photofission and photoneutron data is also readily available from a variety of other sources known to those skilled in the art.

TABLE I

| Type of Interaction | U-233 Threshold | U-235 Threshold | U-238 Threshold | Th-232 Threshold | Pu-239 Threshold |
| --- | --- | --- | --- | --- | --- |
| Photoneutrons ($\gamma$, n), MeV | 5.7 | 5.3 | 6.1 | 6.4 | 5.6 |
| Photofission ($\gamma$, f), MeV | 5.1 | 5.8 | 5.8 | 5.0 | 5.4 |

Since the fission thresholds for all nuclear materials are in the range of from about 5.0 MeV to about 5.8 MeV, scanning a nuclear material with X-ray radiation of at least about 5.8 MeV will induce photofission and delayed neutrons in all such materials. Increasing the energy above the threshold increases the number of delayed neutrons that will be emitted, facilitating detection. 9 MeV may be used, as in the examples, above. Preferably, the delayed neutrons are detected when the X-ray beam is off and after photoneutron emission has ceased. In addition, by this time, X-ray photons that may interfere with counting the delayed neutrons are also not present.

An example of a sequence of operations to detect delayed neutrons due to photofission is now described. First, at time t=0 sec, an electron burst of 9 MeV electrons strikes a target, generating X-ray photons, as is known in the art. These X-ray photons are collimated and projected onto a cargo conveyance under inspection. The electron burst typically lasts a few microseconds. Typical values for the pulse width are between 2.0–4.5 μs. At 1.0–2.0 μs after X-ray photon production ends, a neutron detection system is switched on to detect delayed neutrons from photofission in nuclear materials, if present. The acquisition time period may last up until the point when the next electron burst is about to be sent to the target, typically about 2.5–5.0 milliseconds ("ms") after time t=0. This second burst may be at 9 MeV or at 5 MeV. The neutron detection system may be turned on after each high energy burst, here 9 MeV, for example. In another example, the neutron detectors are turned on only after a TR pixel test indicates the possible presence of HANM in an array of resultant pixels (such as after scanning at both energy endpoints, TR calculation, and analysis of the results, as discussed above).

Photofission results may be analyzed for an entire cargo conveyance or only for a suspect area of the cargo conveyance. A suspect area may be a resultant pixel or a group of resultant pixels with TRs below the threshold, indicating that HANM may be present. In one example, the identification of the suspect area may have a sensitivity and specificity that is not acceptable, prompting further testing. In another example, photofission results may be analyzed if HANM is identified with an acceptable sensitivity and specificity, to determine whether SNM or other nuclear material is present.

Detection of any delayed neutrons indicates that nuclear materials are present within the cargo conveyance. The general location of such nuclear materials may also be identified, as is known in the art. In addition, the identity of the nuclear material may be determined. Experimental counts of a number of delayed neutrons generated by inducing photofission in SNMs at different peak energies and the delayed neutrons' decay times may be organized in five or six ranges, each corresponding to a particular nuclear material. Comparison of the delayed neutron count of the object being tested with these ranges enables identification of a particular nuclear material (and its atomic number). Real-time delayed neutron counting and neutron detection technology are known in the art. See, for example, Tsahi Gozani, Active Non-Destructive Analysis of Nuclear Materials (National Technology Information Service 1981), pp. 173–205.

If further confirmation that a nuclear material, such as an SNM, is present at a particular location within a cargo conveyance is necessary (for example, before a manual inspection is performed), another photofission reaction may be induced at the peak range of photofission energy of nuclear materials, between 13 MeV and 15 MeV. This third scan performed at the higher energy level maximizes the number of delayed neutrons generated by photofission, facilitating neutron detection. The high energy radiation beam may be provided by a separate source or the same source that generates radiation at the other energy endpoints.

Figure 15A:
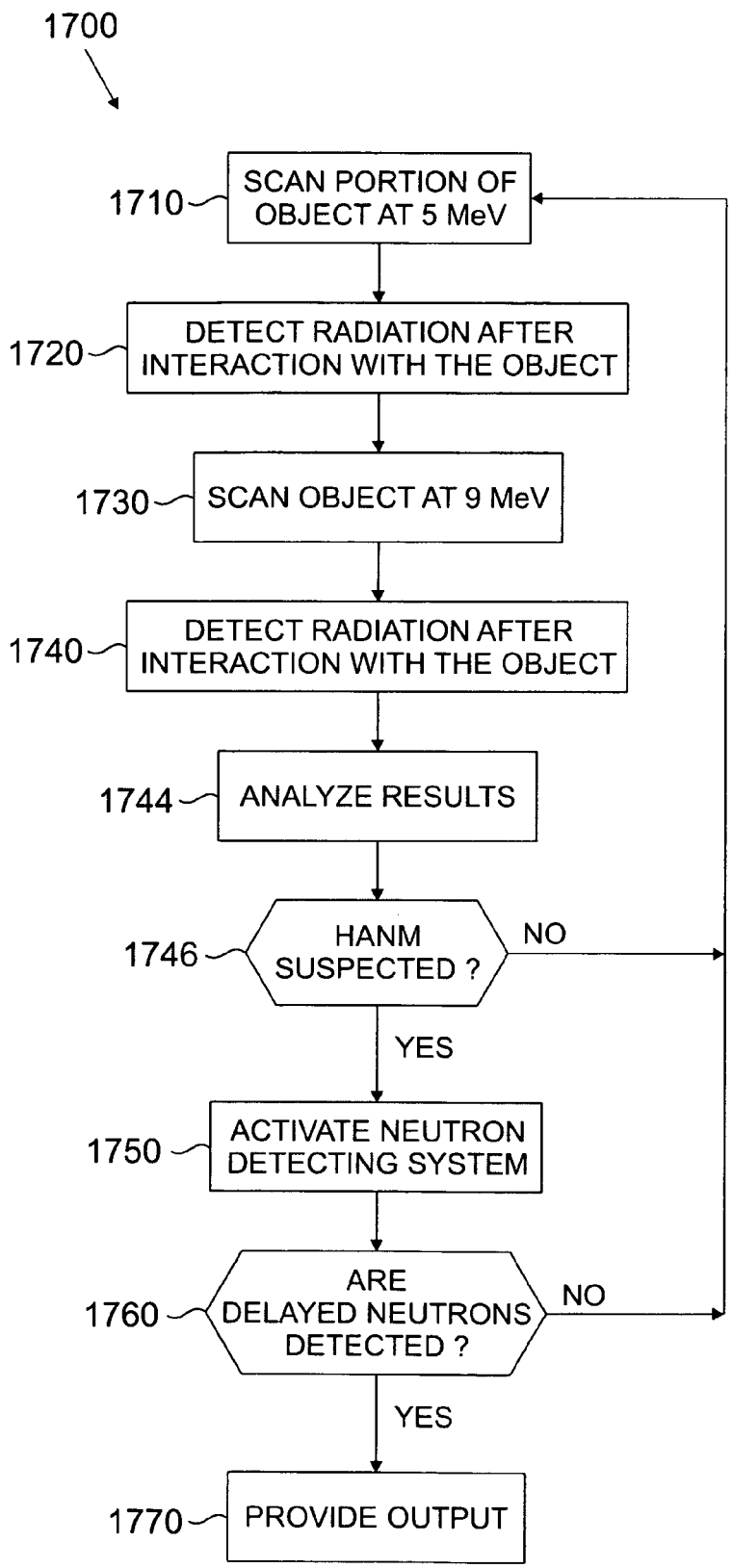
FIG. 15a is an example of a method for examining an object for nuclear materials.

FIG. 15a is an example of a method 1700 for conducting the neutron test. A portion of an object is scanned by radiation having a low energy endpoint, such as 5 MeV, for example, in Step 1710. Radiation is detected after interaction with the object, in Step 1720. A corresponding portion of the object is scanned with radiation having a high energy endpoint, such as 9 MeV, in Step 1730, and radiation is detected after interaction with the object, in Step 1740. The portions of the object may be the portions of the object traversed by a radiation beam at each radiation endpoint. For example, if the radiation beam is in the shape of a fan beam, then each portion of the object is the slice or slices of the object traversed by the two radiation beams. The scanning may cycle between 5 MeV and 9 MeV radiation beams until a sufficient number of pixels covering a sufficient area are collected to conduct one of the tests discussed above or other tests.

The results are analyzed, in Step 1744. The analysis may comprise any of the tests, discussed above. HANM identification for one pair of corresponding portions may be performed quickly enough to decide whether to turn on the neutron detector system. Alternatively, the presence of one pixel indicative of the presence of an HANM or a sufficient number of pixels indicative of the presence of an HANM with a desired sensitivity and specificity in accordance with the tests described above, may cause activation of the neutron detection system.

If HANM is not suspected, then the method 1700 is repeated for another portion of the object.

If HANM is suspected, in Step 1746, then a neutron detection system is activated, in Step 1750. As discussed above, the neutron detection system is preferably activated 1.0–2.0 µs after scanning at 9 MeV (in this example) ends.

It is then determined whether delayed neutrons are detected, in Step 1760. If so, an output indicative of the presence of delayed neutrons is provided, in Step 1770. If not, the method 1700 is repeated for another portion of the object. If the entire object has been scanned, then an output indicative of the failure to detect delayed neutrons may also be provided.

The nuclear test may be conducted if the presence of HANM or nuclear material is suspected after any other test, including the tests described above and others known in the art. For example, a dual energy ratio test, as described in U.S. Pat. No. 5,524,133, which is incorporated by reference herein, may be conducted first to preliminarily identify the actual material content of the object, to determine whether the object at least potentially contains a particular nuclear material. U.S. Pat. No. 5,524,133 is described in more detail above. Such a dual energy test may be conducted in Step 1744 in the method 1700 of FIG. 15a, for example. A test may be conducted at only one energy endpoint, as well. The initial test or tests may involve automatic analysis of results and/or visual analysis of one or more images. The nuclear test may also be conducted after a manual inspection, if an object that is found cannot be identified.

Figure 15B:
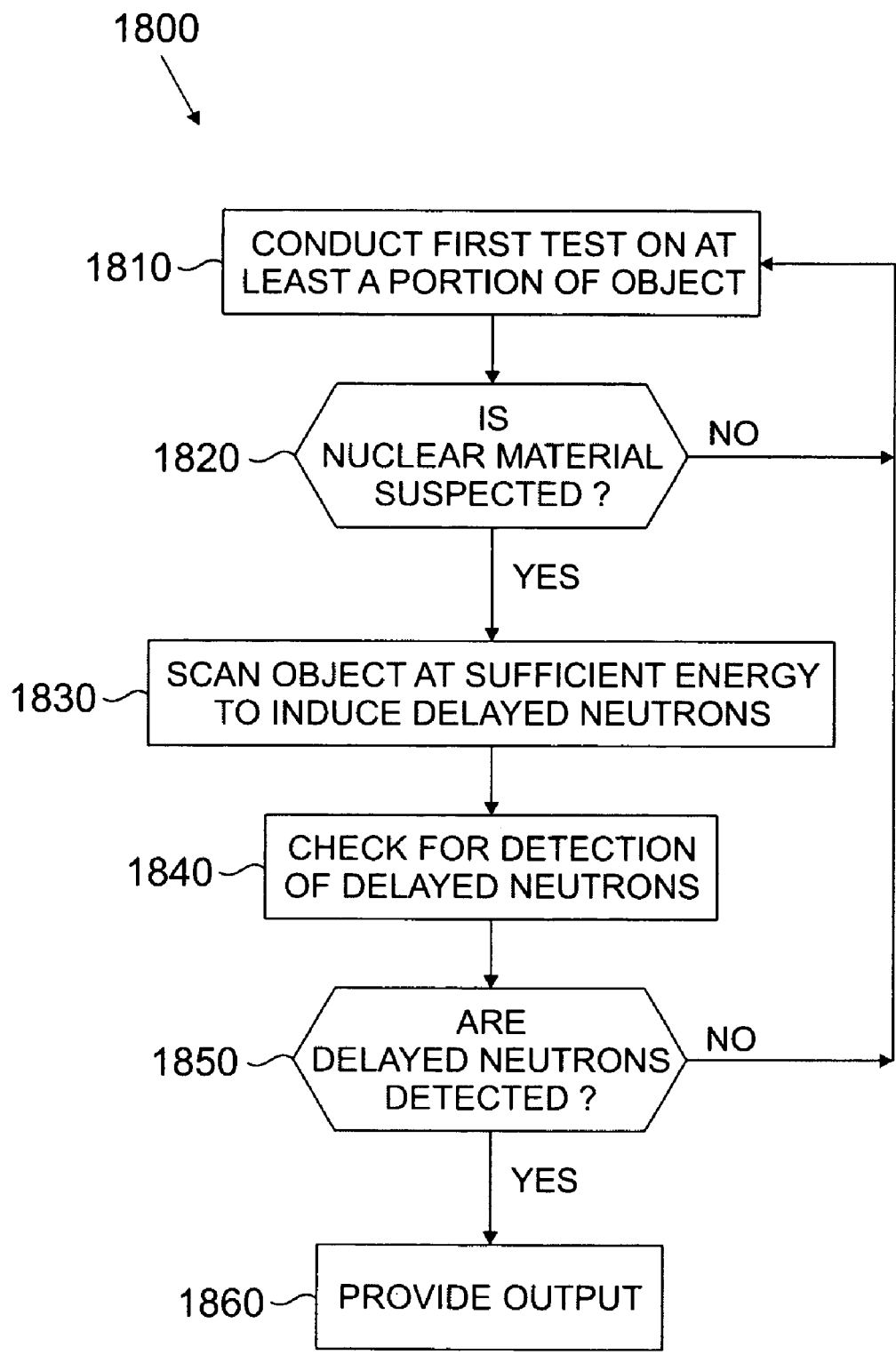
FIG. 15b is an example of a method for examining an object.

FIG. 15b is an example of a method 1800 in accordance with this embodiment. A first test is conducted on at least a portion of an object, in Step 1810. It is then determined if nuclear material is at least suspected, in Step 1820. If not, if remaining portions of the object need to be tested, the method returns to Step 1810. If the entire object has been scanned, an output indicative of the lack of suspicion the presence of nuclear material may be provided.

If nuclear material is suspected, the object is scanned at sufficient energy to induce delayed neutrons, in Step 1830, in order to conduct a nuclear test. A radiation beam with an energy endpoint of at least 5.8 MeV may be used. The detection of delayed neutrons is then checked, in Step 1840. If delayed neutrons are detected, in Step 1850, then an output of the results indicative of the identification of the presence of nuclear material is provided, in Step 1860. If no delayed neutrons are detected in Step 1850, then the method returns to Step 1810 to scan another portion of the object. If the entire object has been scanned and not delayed neutrons detected, a suitable output may be provided, as well. If a high enough energy is used in the first test in Step 1810, then it may not be necessary to conduct Step 1830.

Scanning Systems

Figure 16:
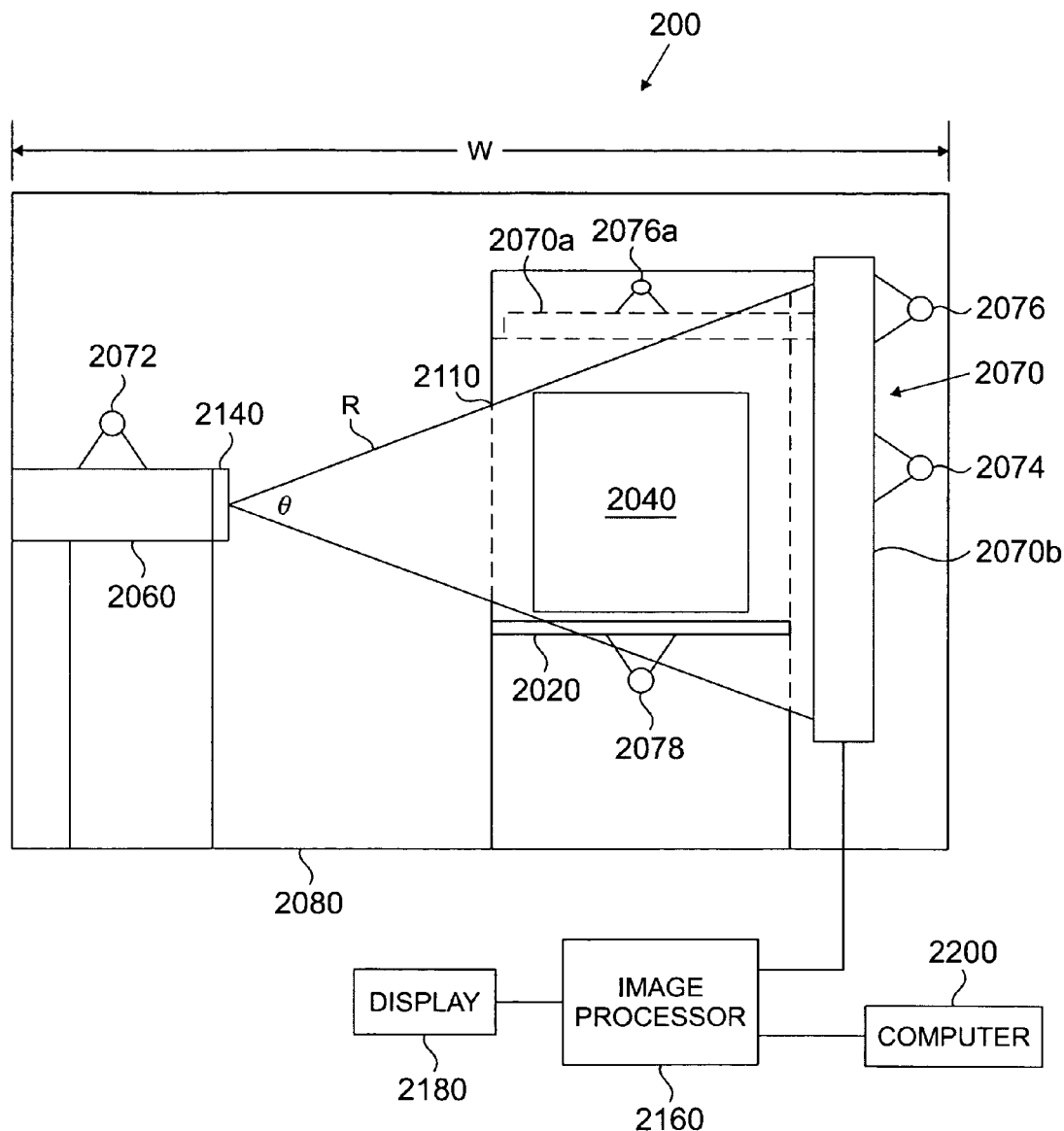
FIG. 16 is a front view of a cargo scanning system programmed to implement embodiments of the invention.

FIG. 16 is a front view of an example of cargo scanning system 2000 programmed to implement embodiments of the invention. A conveyor system 2020 supports and conveys a cargo conveyance 2040 through the scanning system 100, between an X-ray source 2060 and a detector 2070. The conveyor system 2020 may be a mechanically driven conveyor belt, a track or mechanically driven rollers, for example. The X-ray source 2060 directs a radiation beam R of Bremsstrahlung X-ray radiation towards the cargo conveyance 2040. Shielding walls 2080 surround the source 2060 and the detector 2070. The conveyor system 2020 extends through openings in the shielding walls 2080 to allow for the entry and exit of the cargo conveyance 2040.

The cargo conveyance 2040 is conveyed by the conveyor system 2020 through a shielded tunnel 2100. The tunnel 2100 has a first window 2110 and a second window 2120 to allow for the passage of the X-ray radiation beam R from the X-ray source 2060 to the cargo conveyance 2040 and from the cargo conveyance 2040 to the detector array 2070. If the radiation beam R intercepts the conveyor system 2040 and the conveyor system 2020 is a belt or track, a material that causes low attenuation of radiation may be used for the belt or track. If the conveyor system 2020 comprises rollers, a gap may be provided among the plurality of rollers, where necessary. A window may also be provided in the structure supporting the conveyor system 2020, if necessary. Collimators (not shown) may be provided between the cargo conveyance 2040 and the detector 2070 to block scattered radiation from reaching the detector. The conveyor system 2020 may be reversed to examine a portion of the cargo conveyance 2040 or the entire cargo conveyance again. As discussed further below, the cargo conveyance 2040 may be irradiated with multiple energies by rapidly cycling the source 2060 between two energy endpoints as the cargo conveyance 104 is being conveyed through the scanning unit 2000 or by providing two adjacent sources, for example.

A collimator 2140 extends from the end of the X-ray source 2060. The collimator 2140 includes a slot (not shown) shaped to collimate the X-ray beam emitted by the X-ray source 2060 into a desired shape, such as into a fan beam or a cone beam. The slot may have a vertical arc ranging from less than 1 degree to about 50 degrees to define a vertical fan beam having an arc θ and ranging from about 5 degrees to about 45 degrees to define a cone beam, for example. The slot may have other shapes, as well.

The detector 2070 is electrically coupled to an image processor 2160, which is coupled to a display 2180. The image processor 2160 comprises analog-to-digital conversion and digital processing components, as is known in the art. A processor, such as a computer 2200, is electrically coupled to and controls the operation of one or more of the X-ray source 2060, the detector array 2040, the conveyor system 2020, the image processor 2160, and the display 2180. Connections between the processor 122 and all the components are not shown, to simplify the Figure. The processor 2200 may be programmed to implement any or all of the tests described above. The processor 2200 may provide some or all of the processing functions of the image processor 2160. While one processor 2200 is shown, additional processors or computers may be provided, as well. The image processor 2160, the computer 2200 and the display 2180 may be arranged and connected differently. The image processor 2160 may be part of the computer, for example. The computer may be programmed in software and/or hardware to conduct any or all of the tests described above. In one example, the programs may be implemented through an Application Specific Integrated Circuit (ASIC) for example.

Figure 19:
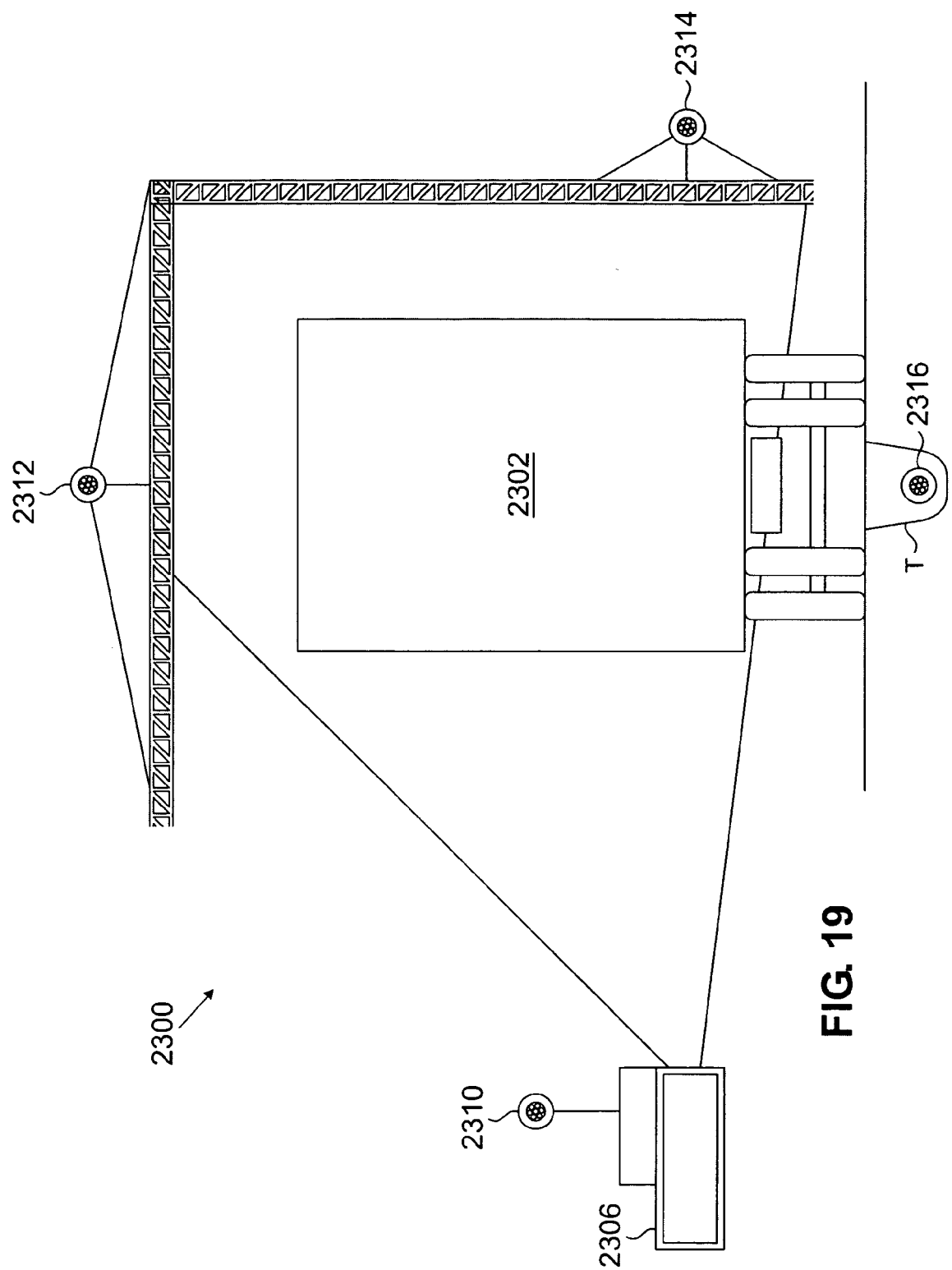
FIG. 19 is a rear view of the system of FIG. 18.

The detector 2070 may be a detector array. The configuration of the detector 2070 may depend on the shape of the collimated radiation beam R. For example, if the radiation beam R is collimated into a fan beam, a one-dimensional detector array 2040 may be provided, comprising a single row of detector elements. If the collimated radiation beam is a cone beam, such as an asymmetric pyramidal cone beam, the detector array may be a two dimensional detector array 2040 comprising two or more adjacent rows of detector elements. The detector array 2040 may comprise a plurality of modules of detectors, each comprising one or more rows of detector elements supported in a housing, as is known in the art. The detector or detector array may be straight or L-shaped. A horizontal arm 2070a of an L-shaped detector array is shown in phantom in FIG. 16. FIG. 19, discussed below, also shows an L-shaped detector. If an L-shaped detector is used in FIG. 16, the source 2060 may be positioned at a lower vertical position, the radiation beam R would intercept more of the horizontal arm 2070a and the vertical portion 2070b of the detector 2070 may be shorter.

The detector 2070 may be a photon detector, such as a photodiode detector array comprising inorganic scintillators, as is known in the art. Cadmium tungstate ($CdWO_4$) scintillators may be used, for example. Amorphous silicon (aSi) detectors, such as PaxScan™ detectors available from Varian Medical Systems, Inc., Palo Alto, Calif., may also be used.

Neutron detectors 2072, 2074, 2076, and 2078 are preferably positioned at multiple locations around the cargo container to detect the neutrons, which are emitted isotropically in all directions. The neutron detector 2072 may be supported by the source, for example. The neutron detector 2074 may be supported by the detector 2070. The neutron detector 2076 may be supported by the upper portion of the detector 2070 or by a vertical arm of an L-shaped detector (see 2076a). The neutron detector 2078 may be supported by the conveyor system 2020 or some other part of the scanning system, below the cargo conveyance 2040.

The neutron detectors 2072–2078 may be cylindrical proportional counters filled with $^3$He. They may have useful lengths of approximately 15–25 cm for use with cargo conveyances 2040, for example. In one example, the counters are covered with cadmium (Cd) and polyethylene layers. The layer of cadmium is used to absorb thermal neutrons which are "slow" neutrons. Fast neutrons are thermalized in the polyethylene layer before being detected in the $^3$He detectors. Only the delayed neutrons are therefore detected in the $^3$He detectors. Suitable neutron detectors are commercially available from Canberra Industries, Meriden, Conn., for example.

Figure 17:
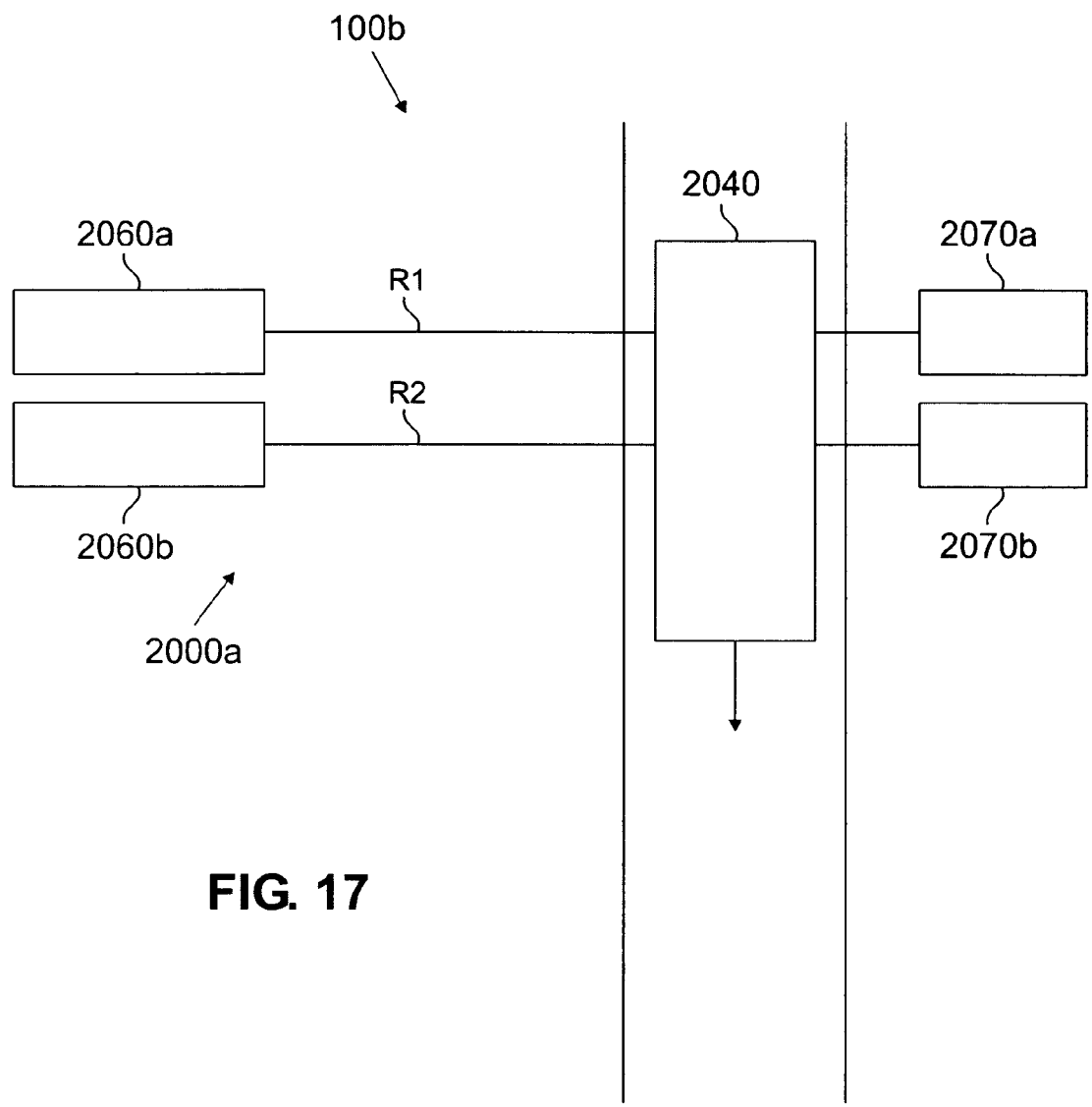
FIG. 17 is a top view of a portion of a cargo scanning system similar to the system of FIG. 15, showing two adjacent sources of X-ray radiation.

FIG. 17 is a top view of a portion of an example of a cargo scanning system 2000a, showing two, adjacent radiation sources 2060a, 2060b, each to generate radiation having a different energy endpoint. Elements common to the system 2000 of FIG. 16 are commonly numbered. The conveyor system 2020 supports and conveys a cargo conveyance 2040 through the scanning system 2000a, between the first X-ray source 2060a and a first detector 2070a, and between the second X-ray source. 2060b and a second detector 2070b. The X-ray sources 2060a and 2060b direct radiation beams R1, R2 towards the cargo conveyance 2040. The X-ray source 2060a may generate a first radiation beam R1 with a first X-ray energy endpoint of 5 MeV, for example, and the X-ray source 2060b may generate a second radiation beam R2 with a second energy endpoint of 9 MeV, for example, or vice-versa. The X-ray sources 2060a and 2060b are positioned at the same angle with respect to the cargo conveyance 2040 and on the same horizontal plane. They may be immediately adjacent to or may be situated apart from each other. They may also be positioned one above the other. It is believed that in a system with two sources, a 40-foot container may be examined in about 30 to 60 seconds.

To examine cargo conveyances 2040 having a width greater than about 5 feet (1.5 meters), the X-ray sources 2060a, 2060b preferably generate radiation having energy endpoints greater than about 1 MeV. 5 MeV and 9 MeV may be used, for example, as discussed above. Other examples of energy endpoints for cargo conveyances having a width greater than about 5 feet (1.5 meters) include 1 MeV and 9 MeV, and 5 MeV and 15 MeV, for example. In order to conduct the neutron test, one of the energy endpoints needs to be at least 5.8 MeV. The X-ray source may be a linear accelerator, such as a Linatron® Linear Accelerator ("Linatron®"), having an accelerating potential at an appropriate level or levels, available from Varian Medical Systems, Inc., Palo Alto, Calif. ("Varian"), for example. In the Varian Linatron®, 360 pulses are output per second. The Varian Linatron® has an opening angle of about 20–30 degrees, for example. Other X-ray sources may be used as well, such as electrostatic accelerators, microtrons and betatrons, for example. The source or sources may also include carbon-12 (C-12), cobalt-60 (Co-60), plutonium-beryllium (Pu—Be), and/or americium-beryllium (Am—Be) based sources. In examining objects having a width less than about 5 feet (1.5 meters), X-ray tubes emitting energy in the keV range may also be used. One energy below 1 MeV and one above 1 MeV may be used for such smaller objects. For example, 600 keV and 5 MeV may be used. Both energies may also be below 1 MeV. For example, 120 keV and 200 keV may be used, as long as the radiation will penetrate through the object being examined.

A single X-ray beam having a single energy endpoint may also be used, with a single energy sensitive detector array to separately detect high and low portions of the energy spectrum, as described in U.S. Pat. No. 5,682,411 and U.S. Pat. No. 6,438,201 B1, for example, which are incorporated by reference, herein. As described in these patents, different portions of the detector array such as alternate lines, may be more sensitive to radiation of one or the other energy.

A single radiation source that switches between energy endpoints may also be used. A description of a suitable source may be found in U.S. application Ser. No. 10/957,212 for a Standing Wave Particle Beam Accelerator, filed on Oct. 1, 2004, which is assigned to the assignee of the present inventor and is incorporated by reference herein. Other linear accelerators that may be used in the present invention are also described in U.S. Pat. No. 6,366,021 B1, U.S. Pat. No. 4,400,650, and U.S. Pat. No. 4,382,208, which are also assigned to the assignee of the present invention and are incorporated by reference herein. Techniques for switching between energies using mechanical switches, such as relays, and other types of switches, such as solid state switches, are known. Switching speeds of about 100 milliseconds may be achieved, for example, to scan a cargo conveyance 20 feet (6.1 meters) long in several minutes.

In another example, the techniques described above may be used in a mobile system for real-time inspection of the cargo conveyances carried by trucks and tractor trailers. The test may be conducted at a highway rest stop, for example. The system may comprise two telescopic tractor trailers, as described in U.S. application Ser. No. 10/455,864 ("the '864 application"), filed on Jun. 6, 2003, which is assigned to the assignee of the present invention and is incorporated by reference herein. In one example described in the '864 application, one telescopic tractor carries the X-ray source or sources. The other telescopic trailor carries the X-ray photon detector and data analysis equipment. The telescoping trailers may be driven to an inspection site in a telescoped, compressed state, expanded at the site, and set up for scanning. A truck to be inspected may then park between the trailers. The source and the detector are then moved across the expanded telescoping section of the respective trailers in unison, to scan the cargo conveyance.

Figure 18:
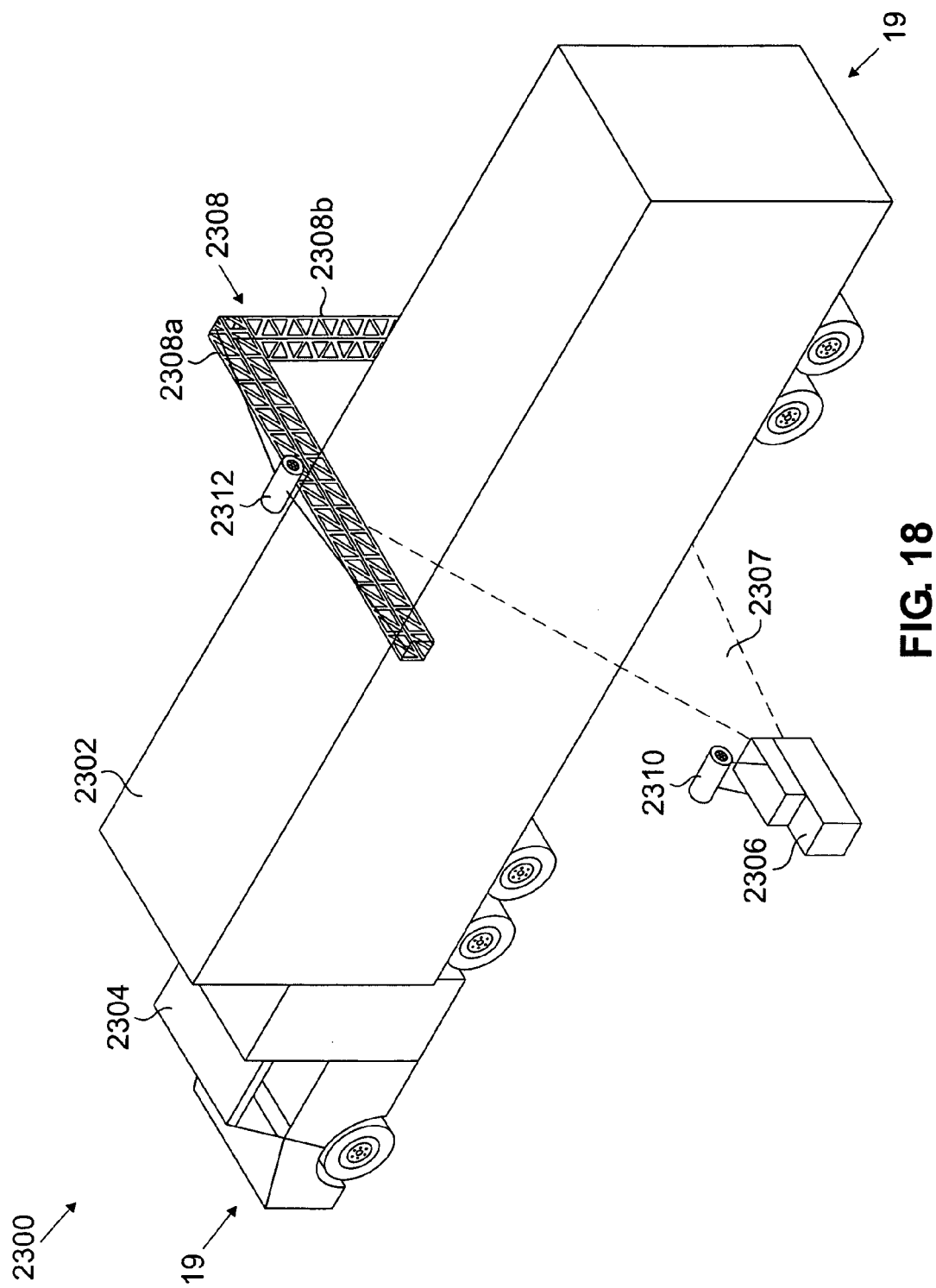
FIG. 18 is a schematic, perspective view of another X-ray scanning system that may implement the embodiments of the invention.

FIG. 18 is a schematic representation of a perspective view of a mobile scanning system 2300 described in the '864 application. The cargo conveyance 2302 is carried by a truck or tractor traitor 2304. The source 2306 emitting a fan beam 2307 and a portion of an L-shaped photon detector 2308 comprising a horizontal portion 2308a and a vertical portion 2308b, are also shown. The telescoping trailers supporting the source 2306 and the detector 2308 are not shown, to simplify the figure. One neutron detector 2310 is supported by the source 2306, another neutron detector 2312 is supported by a horizontal portion 2308a of the detector 2308, and another neutron detector 2314 (shown in FIG. 19) is supported by the vertical portion 2308b of the detector.

FIG. 19 is a rear schematic view of the system 2300 along line 19—19 of FIG. 18. Common elements are commonly numbered. An additional neutron detector 2314 is supported by a vertical arm 2308b. Another neutron detector 2316 may be placed in a trench T in the ground G beneath the position of the cargo conveyance 2302 when the truck or trailer is parked. A vertical detector 2304 may also be used, as shown in the '864 application. In that case, the neutron detector 2314 may be supported at or near the top of the vertical detector, for example. The detectors 2308–2316 may be coupled to a processor or computer as shown and described above, programmed to implement the tests of any or all of the embodiments described above. The source 2606 may be a single source producing alternating 9 MeV and 5 MeV X-ray radiation beams, for example. Two sources may also be stacked or placed next to each other, one to produce a first energy radiation beam and the other to produce a second energy radiation beam, for example. Any or all of the tests described above may be used to automatically detect HANM and nuclear materials, such as SNMs.

While the invention is particularly suited for scanning cargo conveyances for contraband, the invention may be readily adapted to scan other objects, such as luggage and carry-on bags in airports and seaports, as well.

In addition, while an X-ray source or sources are described in the examples above, the source or sources may provide other types of radiation, such as a time delayed neutron beam or gamma rays, for example.

In the examples above, the transmission of the higher energy radiation (9 MeV, for example) through the cargo conveyance is divided by the transmission of the lower energy radiation (5 MeV, for example) through the cargo conveyance to yield the TR and the test criterion for a potential HANM is that the TR is less than the threshold. However, as mentioned above, the transmission at the lower energy radiation may be divided by the transmission at the higher energy radiation, in which case a TR above the threshold would be considered to be a potential HANM, in all the examples, above. In addition, TRs may be calculated based on radiation attenuation instead of radiation transmission at the two energy endpoints.

One of ordinary skill in the art will recognize that other changes may be made to the embodiments described herein without departing from the spirit and scope of the invention, which is defined by the claims, below.

What is claimed is:

1. A method of examining contents of an object, the method comprising:
   scanning first portions of the object with a first radiation beam at a first energy;
   detecting first radiation after interaction of the first radiation beam with the first portions, wherein projections of at least a portion of the first radiation beam through each portion, onto a detector, define respective first pixels;
   scanning second portions of the object with a second radiation beam at a second energy different than the first energy;
   detecting second radiation after interaction of the second radiation beam with the second portions, wherein projections of at least a portion of the second radiation beam through each portion, onto a detector, define respective second pixels;

calculating first functions of the radiation detected at the first and second energies, for corresponding first and second pixels;

grouping first functions of a plurality of corresponding pixels into at least one group;

calculating a second function based, at least in part, on the first functions of at least certain of the plurality of pixels in the at least one group; and determining whether the object at least potentially contains material having a high atomic number ("high atomic number material") greater than a predetermined atomic number, based, at least in part, on the second function of the at least one group.

2. The method of claim 1, further comprising:
comparing the first functions to a criterion based, at least in part, on the predetermined atomic number, prior to calculating the second function;
wherein calculating the second function is based, at least in part, on the first functions meeting the criterion.

3. The method of claim 2, comprising:
grouping first functions of corresponding pixels into at least one examination window having a predetermined size;
calculating the second function by counting a number of first functions within the examination window that meet the criterion; and
comparing the counted number to a predetermined number to determine whether the object at least potentially contains a high atomic number material.

4. The method of claim 3, wherein:
the predetermined number is based, at least in part, on a predetermined false positive rate.

5. The method of claim 2, wherein:
the first energy is greater than the second energy;
calculating the first function comprises dividing the first radiation by the second radiation; and
corresponding pixels meeting the criterion have first functions less than the threshold.

6. The method of claim 2, wherein:
the first energy is less than the second energy;
calculating the first function comprises dividing the first radiation by the second radiation; and
corresponding pixels meeting the criterion have first functions greater than the threshold.

7. The method of claim 2, comprising:
grouping first functions of contiguous corresponding pixels that meet the criterion;
calculating an area of the grouping; and
comparing the area with a predetermined area to determine whether the object at least potentially contains a high atomic number material.

8. The method of claim 2, wherein the at least one grouping defines at least one matrix and the second function is an average, the method comprising:
calculating an average of the first functions for the plurality of corresponding pixels within the at least one matrix; and
comparing the average to the criterion to determine whether the object at least potentially contains a high atomic number material.

9. The method of claim 8, wherein comparing the first functions to the criterion comprises:
comparing the first function to a threshold.

10. The method of claim 9, further comprising:
calculating the threshold, at least in part, by:
scanning at least a portion of a second object comprising material having an atomic number equal to the predetermined atomic number, with a third radiation beam at the first energy;
detecting third radiation after interaction of the third radiation beam with the at least a portion of the second object;
scanning at least a portion of the second object with a fourth radiation beam at the second energy;
detecting fourth radiation after interaction of the fourth radiation beam with the at least a portion of the second object; and
calculating the first function of the radiation detected at the third and fourth energies.

11. The method of claim 10, wherein scanning at least a portion of the second object comprises:
scanning at least a portion of a second object comprising a material having an atomic number less than an atomic number of uranium.

12. The method of claim 11, comprising:
scanning at least a portion of a second object comprising a material having an atomic number less than an atomic number of lead.

13. The method of claim 12, comprising:
scanning at least a portion of a second object chosen from the group consisting of iron, copper, and nickel.

14. The method of claim 12, comprising:
scanning at least a portion of a second object comprising plastic.

15. The method of claim 10, comprising:
scanning a plurality of objects comprising a plurality of different materials to calculate a plurality of thresholds; and
selecting a threshold for use in the criterion based, at least in part, on the expected contents of the object.

16. The method of claim 1, comprising:
detecting the first radiation and the second radiation by detector elements of a detector;
wherein first radiation and second radiation detected by a single detector element defines a first and second pixel, respectively.

17. The method of claim 16, wherein:
projections resulting in first and second pixels are derived from projections through portions of the object that overlap by at least one-half.

18. The method of claim 1, further comprising:
selecting a threshold based on radiation detected at at least one of the first radiation and the second radiation.

19. The method of claim 1, further comprising:
comparing the second function to a predetermined criteria independent of the object; and
determining whether the object at least potentially contains high atomic number based, at least in part, on the comparison.

20. A method of examining contents of an object, the method comprising:
scanning first portions of the object with a first radiation beam at a first energy;
detecting first radiation after transmission of the first radiation beam through the first portions, wherein projections of at least a portion of the first radiation beam through each first portion, onto a detector, define respective first pixels;
scanning second portions of the object with a second radiation beam at a second energy;

detecting second radiation resulting from transmission of the second radiation beam through the second portions, wherein projections of at least a portion of the second radiation beam through each second portion, onto a detector, define respective second pixels;

calculating ratios between functions of the first radiation and functions of the second radiation for each of a plurality of pairs of corresponding first and second pixels, each pair of corresponding pixels resulting in a resultant pixel having the respective ratio;

storing the respective ratios in an array comprising rows and columns corresponding to the resultant pixels;

comparing the respective ratios with a threshold that is a function of a predetermined atomic number;

selecting at least one examination window comprising a plurality of rows and columns of respective ratios;

determining whether the object at least potentially contains material having an atomic number greater than the predetermined atomic number based, at least in part, on whether a predetermined number of respective ratios in each of the at least one examination windows meeting criterion with respect to the respective ratios and the threshold, is greater than a predetermined number.

21. The method of claim 20, wherein the predetermined number is based, at least in part, on a predetermined false positive rate.

22. The method of claim 20, wherein the size of the examination window corresponds to a size of a material capable of a self-sustaining nuclear reaction.

23. The method of claim 20, wherein:
corresponding first and second pixels are derived from projections through portions of the object overlapping by at least one-half.

24. A method of examining contents of an object, the method comprising:
scanning first portions of the object with a first radiation beam at a first energy;
detecting first radiation resulting from transmission of the first radiation beam through the first portions, wherein projections of the first radiation beam through each first portion, onto a detector, define respective first pixels;
scanning second portions of the object with a second radiation beam at a second energy;
detecting second radiation resulting from transmission of the second radiation beam through the second portions, wherein projections of the second radiation beam through each second portion, onto a detector, define respective second pixels;
calculating ratios between functions of the first detected radiation and functions of the second detected radiation, for a plurality of pairs of corresponding first and second pixels, each pair of corresponding pixels defining a resultant pixel having the respective ratio;
comparing the ratios for the resultant pixels with a threshold that is a function of a predetermined atomic number;
identifying at least one group of contiguous resultant pixels whose respective ratios meet a criterion with respect to the threshold;
comparing an area covered by each of the at least one group with a predetermined area; and
determining whether the object at least potentially contains a material having an atomic number greater than the predetermined atomic number based, at least in part, on the second comparison.

25. The method of claim 24, wherein the predetermined area corresponds to a size of a high atomic number material capable of a self-sustaining nuclear reaction.

26. The method of claim 24, further comprising:
calculating an average ratio of a plurality of contiguous pixels;
comparing the average to the threshold; and
determining whether the object at least potentially contains material having an atomic number greater than the predetermined atomic number based, at least in part, on the comparison.

27. The method of claim 24, wherein:
corresponding first and second pixels overlap by at least one-half of their respective areas.

28. A method of examining contents of an object, the method comprising:
scanning first portions of the object with a first radiation beam at a first energy;
detecting first radiation resulting from transmission of the first radiation beam through the first portions, wherein projections of at least a portion of the first radiation beam through each first portion, onto a detector, define respective first pixels;
scanning second portions of the object with a second radiation beam at a second energy;
detecting second radiation resulting from transmission of the second radiation beam through the second portions, wherein projections of at least a portion of the second radiation beam through each second portion, onto a detector, define respective second pixels;
calculating ratios between functions of the first detected radiation and functions of the second detected radiation, for a plurality of pairs of corresponding first and second pixels, each pair of corresponding pixels resulting in a respective resultant pixel having the respective ratio;
comparing the ratios of the resultant pixels with a threshold which is a function of a predetermined atomic number;
grouping a plurality of resultant pixels;
calculating a function of the ratios of the grouping;
comparing the function with the threshold; and
determining whether the object at least potentially contains material having an atomic number greater than the predetermined atomic number based, at least in part, on the second comparison.

29. The method of claim 28, wherein the function is an average or a median.

30. The method of claim 28, further comprising:
selecting a resultant pixel having a ratio meeting a criterion with respect to the ratio and the threshold; and
grouping the plurality of pixels with respect to the selected pixel.

31. The method of claim 30, comprising:
grouping the plurality of contiguous resultant pixels into a matrix centered about the selected resultant pixel.

32. The method of claim 31, further comprising:
calculating a second average of the ratios for a second matrix, the second matrix being centered about the selected resultant pixel and being larger than the first matrix;
comparing the second average with the threshold; and
determining whether the object at least potentially comprises a high atomic number material based, at least in part, on the second and third comparisons.

33. The method of claim 28, wherein:
corresponding first and second pixels are derived from projections through portions of the object overlapping by at least one-half of their respective areas.

34. The method of claim 28, wherein the predetermined area corresponds to a size of a high atomic number material capable of a self-sustaining nuclear reaction.

35. A system for examining contents of an object, the system comprising:
at least one radiation source to scan at least a portion of an object with first and second radiation beams at first and second radiation energies, respectively, wherein the first radiation energy is different than the second radiation energy;
at least one detector positioned to detect radiation at the first and second radiation energies after interaction with the object, wherein projections of at least a portion of the first and second radiation beams through each portion onto the detector, define respective first and second pixels;
at least one processor coupled to the detector, the at least one processor being programmed to:
calculate first functions of the radiation detected at the first and second energies, for corresponding first and second pixels;
group first functions of a plurality of corresponding pixels into at least one group;
calculate a second function of the first functions of the plurality of pixels in the at least one group; and
determine whether the object at least potentially contains high atomic number material having an atomic number greater than a predetermined atomic number based, at least in part, on the second function of the at least one group.

36. The system of claim 35, wherein the at least one processor is further programmed to:
compare the first functions to a criterion based, at least in part on the predetermined atomic number, prior to calculating the second function; and
calculate the second function based, at least in part, on first functions meeting the criterion.

37. The system of claim 36, wherein the at least one processor is programmed to:
group first functions of corresponding pixels into at least one examination window having a predetermined size;
calculate the second function by counting a number of first functions within the examination window that meet the criterion; and
compare the counted number to a predetermined number to determine whether the object at least potentially contains a high atomic number material.

38. The system of claim 37, wherein:
the predetermined number is based, at least in part, on a predetermined false positive rate.

39. The system of claim 36, wherein the at least one processor is programmed to:
group first functions of contiguous corresponding pixels that meet the criterion;
calculate an area of the grouping; and
compare the area of the grouping with a predetermined area to determine whether the object at least potentially contains a high atomic number material.

40. The system of claim 36, wherein the at least one grouping defines at least one matrix and the second function is an average, the at least one processor being programmed to:
calculate an average of the first functions for the plurality of corresponding pixels within the at least one matrix; and
compare the average of the at least one matrix to the criterion to determine whether the object at least potentially contains a high atomic number material.

41. The system of claim 36, wherein the criterion comprises a threshold.

42. The system of claim 41, wherein the at least one processor is further programmed to:
calculate the threshold based, at least in part, on detected radiation after scanning a test material having an atomic number equal to the predetermined atomic number, at the first and second radiation energies.

43. The system of claim 42, wherein the at least one processor is further programmed to:
select a threshold for use in a criterion based, at least in part, on expected contents of the object.

44. A method of examining contents of an object, the method comprising:
scanning first portions of the object with a first radiation beam at a first energy;
detecting first radiation after interaction of the first radiation beam with the first portions;
scanning second portions of the object with a second radiation beam at a second energy different than the first energy;
detecting second radiation after interaction of the second radiation beam with the second portions;
calculating first functions of the radiation detected at the first and second energies, for corresponding first and second portions;
grouping first functions of a plurality of corresponding first and second portions into at least one group;
calculating a second function based, at least in part, on the first functions of at least certain of the plurality of corresponding first and second portions in the at least one group; and
determining whether the object at least potentially contains high atomic number material having an atomic number greater than a predetermined atomic number, based, at least in part, on the second function of the at least one group.

45. The method of claim 44, wherein the predetermined atomic number is at least 26.

46. The method of claim 45, wherein the predetermined atomic number is at least 74.

47. The method of claim 46, wherein the predetermined atomic number is at least 92.

48. The method of claim 44, further comprising:
comparing the second function to a predetermined criteria independent of the object; and
determining whether the object at least potentially contains high atomic number material based, at least in part, on the comparison.

49. A system for examining contents of an object, the system comprising:
at least one radiation source to scan at least a portion of an object with first and second radiation beams at first and second radiation energies, respectively, wherein the first radiation energy is different than the second radiation energy;

at least one detector positioned to detect radiation at the first and second radiation energies after interaction with the object, wherein projections of at least a portion of the first and second radiation beams through each portion onto the detector, define respective first and second pixels;

at least one processor coupled to the detector, the at least one processor being programmed to:

calculate first functions of the radiation detected at the first and second energies, for corresponding first and second portions;

group first functions of a plurality of corresponding first and second portions into at least one group;

calculate a second function of the first functions of the plurality of first and second portions in the at least one group; and determine whether the object at least potentially contains high atomic number material having an atomic number greater than a predetermined atomic number based, at least in part, on the second function of the at least one group.

50. The system of claim 49, wherein the predetermined atomic number is at least 26.

51. The system of claim 50, wherein the predetermined atomic number is at least 74.

52. The system of claim 51, wherein the predetermined atomic number is at least 92.

53. The system of claim 49, wherein the processor is further programmed to:

compare the second function to a predetermined criteria independent of the object; and determine whether the object at least potentially contains high atomic number material based, at least in part, on the comparison.

* * * * *